US009445971B2

(12) United States Patent
Anderson et al.

(10) Patent No.: US 9,445,971 B2
(45) Date of Patent: Sep. 20, 2016

(54) METHOD OF MANUFACTURING SOLID DOSAGE FORM

(71) Applicant: JOHNSON & JOHNSON CONSUMER INC., Skillman, NJ (US)

(72) Inventors: Oliver Anderson, Glenside, PA (US); Harry S. Sowden, Glenside, PA (US); Gerard P. McNally, Berwyn, PA (US); William J. Stuhl, Burlington, NJ (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 578 days.

(21) Appl. No.: 13/804,229

(22) Filed: Mar. 14, 2013

(65) Prior Publication Data

US 2013/0292884 A1 Nov. 7, 2013

Related U.S. Application Data

(60) Provisional application No. 61/640,910, filed on May 1, 2012, provisional application No. 61/704,773, filed on Sep. 24, 2012.

(51) Int. Cl.
*A61J 3/00* (2006.01)
*A61J 3/10* (2006.01)
(Continued)

(52) U.S. Cl.
CPC .. *A61J 3/10* (2013.01); *A61J 3/00* (2013.01); *A61J 3/06* (2013.01); *A61K 9/2072* (2013.01); *A61K 9/2086* (2013.01);
(Continued)

(58) Field of Classification Search
None
See application file for complete search history.

(56) References Cited

U.S. PATENT DOCUMENTS 2,007,961 A * 7/1935 Bolton ................. B28B 7/0088
216/101
2,183,053 A 12/1939 Taylor
(Continued)

FOREIGN PATENT DOCUMENTS

CN 1119934 A 4/1996
CN 1141589 A 1/1997
(Continued)

OTHER PUBLICATIONS

Int'l Search Report for Application No. PCT/US2008/081496, dated Jul. 15, 2009.
(Continued)

*Primary Examiner* — Edmund Lee

(57) ABSTRACT

In one aspect, the present invention features a method of manufacturing a solid dosage form, the method including the steps of: (a) measuring an amount of a first powder blend within a dosing nozzle, wherein the first powder blend includes a pharmaceutically active agent; (b) discharging the measured amount of a first powder blend from the dosing nozzle into a forming cavity within a die block, the forming cavity having an inner wall, a first opening at the surface of one side of the die block, and a second opening at the surface on the opposite side of the die block; (c) moving a first forming tool into the forming cavity through the first opening of the forming cavity such that the first powder blend is formed into the shape of the dosage form within the forming cavity between the inner wall, the first forming tool and a second forming tool within or adjacent to the cavity; (d) applying RF energy between a first electrode and a second electrode such that the energy heats the first powder blend within the forming cavity to form the dosage form; and (e) removing the dosage form from the forming cavity.

21 Claims, 24 Drawing Sheets

(51) Int. Cl.

| | | |
|---|---|---|
| A61K 9/20 | (2006.01) | |
| A61K 31/137 | (2006.01) | |
| A61K 31/167 | (2006.01) | |
| A61K 31/4545 | (2006.01) | |
| A61J 3/06 | (2006.01) | |

(52) U.S. Cl.
CPC .......... *A61K 9/2095* (2013.01); *A61K 31/137* (2013.01); *A61K 31/167* (2013.01); *A61K 31/4545* (2013.01)

(56) References Cited

U.S. PATENT DOCUMENTS

| | | | |
|---|---|---|---|
| 2,347,971 A * | 5/1944 | Sayre | B30B 11/02 222/429 |
| 2,887,437 A | 5/1959 | Klioze et al. | |
| 3,071,470 A | 1/1963 | Bishop | |
| 3,337,116 A | 8/1967 | Nowak | |
| 3,586,066 A | 6/1971 | Brown | |
| 3,670,065 A | 6/1972 | Eriksson et al. | |
| 3,840,631 A * | 10/1974 | Alexander, Jr. | B30B 11/34 264/113 |
| 3,859,016 A * | 1/1975 | McGee | B22F 7/06 425/130 |
| 3,885,026 A | 5/1975 | Heinemann et al. | |
| 4,054,449 A * | 10/1977 | Dunn | B22F 7/00 419/6 |
| 4,139,589 A * | 2/1979 | Beringer | A61J 3/10 264/131 |
| 4,158,411 A | 6/1979 | Hall et al. | |
| 4,173,626 A | 11/1979 | Dempski et al. | |
| 4,230,693 A | 10/1980 | Izzo et al. | |
| 4,238,431 A | 12/1980 | Stuben et al. | |
| 4,260,596 A | 4/1981 | Mackles | |
| 4,268,238 A | 5/1981 | Marc | |
| 4,268,465 A | 5/1981 | Suh et al. | |
| 4,327,076 A | 4/1982 | Puglia et al. | |
| 4,396,564 A | 8/1983 | Stuben et al. | |
| 4,398,634 A | 8/1983 | McClosky | |
| 4,508,740 A | 4/1985 | McSweeney | |
| 4,526,525 A | 7/1985 | Oiso et al. | |
| 4,590,075 A | 5/1986 | Wei et al. | |
| 4,609,543 A | 9/1986 | Morris et al. | |
| 4,642,903 A | 2/1987 | Davies | |
| 4,684,534 A | 8/1987 | Valentine | |
| 4,758,439 A | 7/1988 | Godfrey | |
| 4,762,719 A | 8/1988 | Forester | |
| 4,777,050 A | 10/1988 | Vadino | |
| 4,824,681 A | 4/1989 | Schobel et al. | |
| 4,828,845 A | 5/1989 | Zamudio-Tena et al. | |
| 4,832,956 A | 5/1989 | Gergely et al. | |
| 4,851,226 A | 7/1989 | Julian et al. | |
| 4,857,331 A | 8/1989 | Shaw et al. | |
| 4,863,742 A | 9/1989 | Panoz et al. | |
| 4,906,478 A | 3/1990 | Valentine et al. | |
| 4,979,720 A | 12/1990 | Robinson | |
| 4,980,170 A | 12/1990 | Schneider et al. | |
| 4,984,240 A | 1/1991 | Keren-Zvi et al. | |
| 4,994,260 A | 2/1991 | Kallstrand et al. | |
| 5,013,557 A | 5/1991 | Tai | |
| 5,046,618 A | 9/1991 | Wood | |
| 5,064,656 A | 11/1991 | Gergely et al. | |
| 5,073,374 A | 12/1991 | McCarty | |
| 5,075,114 A | 12/1991 | Roche | |
| 5,082,436 A | 1/1992 | Choi et al. | |
| 5,109,893 A | 5/1992 | Derby | |
| 5,112,616 A | 5/1992 | McCarty | |
| 5,126,151 A | 6/1992 | Bodor et al. | |
| 5,134,260 A | 7/1992 | Piehler et al. | |
| 5,139,407 A | 8/1992 | Kim et al. | |
| 5,178,878 A | 1/1993 | Webling et al. | |
| 5,215,755 A | 6/1993 | Roche et al. | |
| 5,223,264 A | 6/1993 | Webling et al. | |
| 5,262,171 A | 11/1993 | Login et al. | |
| 5,275,822 A | 1/1994 | Valentine et al. | |
| 5,286,497 A | 2/1994 | Hendrickson et al. | |
| 5,304,055 A | 4/1994 | Van Lengerich et al. | |
| 5,320,848 A | 6/1994 | Greyer et al. | |
| 5,322,655 A * | 6/1994 | Ebey | B07C 5/365 264/109 |
| 5,330,763 A | 7/1994 | Gole et al. | |
| 5,464,632 A | 11/1995 | Cousin et al. | |
| 5,489,436 A | 2/1996 | Hoy et al. | |
| 5,501,858 A | 3/1996 | Fuisz | |
| 5,501,861 A | 3/1996 | Makimo et al. | |
| 5,503,846 A | 4/1996 | Wehling et al. | |
| 5,558,880 A | 9/1996 | Gole et al. | |
| 5,558,899 A | 9/1996 | Kuzee et al. | |
| 5,560,963 A | 10/1996 | Tisack | |
| 5,587,172 A | 12/1996 | Cherukuri et al. | |
| 5,587,179 A | 12/1996 | Gergely et al. | |
| 5,607,697 A | 3/1997 | Alkire et al. | |
| 5,622,719 A | 4/1997 | Myers et al. | |
| 5,631,023 A | 5/1997 | Kearney et al. | |
| 5,635,210 A | 6/1997 | Allen, Jr. et al. | |
| 5,648,093 A | 7/1997 | Gole et al. | |
| 5,653,993 A | 8/1997 | Ghanta et al. | |
| 5,662,849 A | 9/1997 | Bogne et al. | |
| 5,672,364 A | 9/1997 | Kato et al. | |
| 5,720,974 A | 2/1998 | Makino et al. | |
| 5,814,339 A | 9/1998 | Prudhoe | |
| 5,886,081 A | 3/1999 | Sternowski | |
| 5,912,013 A | 6/1999 | Rudnic et al. | |
| 5,939,091 A | 8/1999 | Eoga et al. | |
| 5,997,905 A | 12/1999 | McTeigue et al. | |
| 6,024,981 A | 2/2000 | Khankarti et al. | |
| 6,060,078 A | 5/2000 | Lee | |
| 6,103,260 A | 8/2000 | Luber et al. | |
| 6,224,905 B1 | 5/2001 | Lawrence et al. | |
| 6,227,836 B1 * | 5/2001 | Kato | A61J 3/10 425/100 |
| 6,228,398 B1 | 5/2001 | Devane et al. | |
| 6,258,381 B1 | 7/2001 | Luber et al. | |
| 6,270,805 B1 | 8/2001 | Chen et al. | |
| 6,277,409 B1 | 8/2001 | Luber et al. | |
| 6,284,270 B1 | 9/2001 | Lagoviyer et al. | |
| 6,287,596 B1 | 9/2001 | Murakami et al. | |
| 6,316,026 B1 | 11/2001 | Tatara et al. | |
| 6,322,819 B1 | 11/2001 | Barnside et al. | |
| 6,328,994 B1 | 12/2001 | Shimizu et al. | |
| 6,376,441 B1 * | 4/2002 | Ross | C11D 17/006 510/146 |
| 6,465,010 B1 | 10/2002 | Lagoviyer et al. | |
| 6,499,984 B1 | 12/2002 | Ghebre-Sellassie et al. | |
| 6,569,463 B2 | 5/2003 | Patel et al. | |
| 6,589,554 B1 | 7/2003 | Mizumoto et al. | |
| 6,612,826 B1 | 9/2003 | Bauer et al. | |
| 6,649,888 B2 | 11/2003 | Ryan et al. | |
| 6,753,009 B2 | 6/2004 | Luber et al. | |
| 6,767,200 B2 | 7/2004 | Sowden et al. | |
| 6,814,978 B2 | 11/2004 | Bunick et al. | |
| 6,932,979 B2 | 8/2005 | Gergely | |
| 7,070,825 B2 | 7/2006 | Ndife et al. | |
| 7,122,143 B2 * | 10/2006 | Sowden | A23G 3/04 264/271.1 |
| 7,132,072 B2 | 11/2006 | Ozeki et al. | |
| 7,157,100 B2 | 1/2007 | Doshi et al. | |
| 7,625,622 B2 | 12/2009 | Teckoe et al. | |
| 7,883,330 B2 * | 2/2011 | Inoue | B30B 11/14 425/183 |
| 8,114,328 B2 * | 2/2012 | Sowden | A23G 3/04 264/254 |
| 8,127,516 B2 | 3/2012 | Lee et al. | |
| 8,313,768 B2 | 11/2012 | Kriksunov et al. | |
| 8,343,533 B2 * | 1/2013 | Chen | A61K 9/0056 424/440 |
| 8,673,190 B2 * | 3/2014 | Sowden | A23G 3/04 264/109 |
| 2001/0033831 A1 | 10/2001 | Chow et al. | |
| 2002/0012701 A1 | 1/2002 | Kolter et al. | |
| 2002/0018800 A1 | 2/2002 | Pinney et al. | |
| 2002/0079121 A1 | 6/2002 | Ryan et al. | |
| 2002/0122822 A1 | 9/2002 | Bunick et al. | |
| 2003/0021842 A1 | 1/2003 | Lagoviyer et al. | |

(56) References Cited

U.S. PATENT DOCUMENTS

| | | |
|---|---|---|
| 2003/0068373 A1 | 4/2003 | Luber et al. |
| 2003/0161879 A1 | 8/2003 | Ohmori et al. |
| 2003/0175339 A1 | 9/2003 | Bunick |
| 2003/0194442 A1 | 10/2003 | Guivarch et al. |
| 2003/0224044 A1 | 12/2003 | Weibel |
| 2003/0228368 A1 | 12/2003 | Wynn et al. |
| 2004/0115305 A1 | 6/2004 | Andersen et al. |
| 2004/0137057 A1 | 7/2004 | Sowden et al. |
| 2004/0156902 A1 | 8/2004 | Lee et al. |
| 2004/0191499 A1 | 9/2004 | Hallett et al. |
| 2005/0019407 A1* | 1/2005 | Sowden .......... A23G 1/54 424/472 |
| 2005/0129763 A1* | 6/2005 | Sowden .......... A61K 9/209 424/470 |
| 2005/0138899 A1 | 6/2005 | Draisey et al. |
| 2005/0142188 A1 | 6/2005 | Gillis et al. |
| 2005/0186274 A1 | 8/2005 | Kohlrausch |
| 2006/0034927 A1 | 2/2006 | Casadevall et al. |
| 2006/0134195 A1 | 6/2006 | Fu et al. |
| 2007/0071806 A1 | 3/2007 | McCarty |
| 2007/0184111 A1 | 8/2007 | Harris et al. |
| 2007/0196477 A1 | 8/2007 | Withiam et al. |
| 2007/0281009 A1 | 12/2007 | Kamisono et al. |
| 2008/0286340 A1 | 11/2008 | Andersson et al. |
| 2009/0060983 A1* | 3/2009 | Bunick .......... A61K 9/0056 424/440 |
| 2009/0092672 A1 | 4/2009 | Venkatesh et al. |
| 2009/0110716 A1 | 4/2009 | Bunick et al. |
| 2009/0110717 A1 | 4/2009 | Singh et al. |
| 2009/0311320 A1 | 12/2009 | Oury et al. |
| 2010/0016348 A1 | 1/2010 | Bunick et al. |
| 2010/0016451 A1 | 1/2010 | Bunick et al. |
| 2010/0021507 A1 | 1/2010 | Bunick et al. |
| 2011/0068511 A1* | 3/2011 | Sowden .......... A61K 9/0056 264/449 |
| 2011/0070170 A1* | 3/2011 | Koll .......... A61K 9/0056 424/48 |
| 2011/0070286 A1 | 3/2011 | Hugerth et al. |
| 2011/0070301 A1 | 3/2011 | Luber et al. |
| 2011/0071184 A1 | 3/2011 | Bunick et al. |
| 2011/0071185 A1 | 3/2011 | Bunick et al. |
| 2011/0081184 A1* | 4/2011 | Hayashi .......... B42C 13/00 399/407 |
| 2011/0318411 A1 | 12/2011 | Luber et al. |
| 2011/0319441 A1 | 12/2011 | Szymczak et al. |
| 2011/0319492 A1 | 12/2011 | Luber et al. |
| 2012/0022170 A1 | 1/2012 | Bunick et al. |

FOREIGN PATENT DOCUMENTS

| | | |
|---|---|---|
| CN | 1498080 A | 5/2004 |
| CN | 1578724 A | 2/2005 |
| CN | 1805735 A | 7/2006 |
| CN | 101052373 A | 10/2007 |
| EP | 0 070 127 | 1/1983 |
| EP | 0192460 B1 | 8/1986 |
| EP | 0 416 791 A2 | 3/1991 |
| EP | 0829341 A2 | 3/1998 |
| EP | 1974724 A2 | 10/2008 |
| EP | 2308511 B1 | 12/2012 |
| GB | 772 315 | 4/1957 |
| GB | 1 097 207 | 12/1967 |
| GB | 1538280 A | 1/1979 |
| JP | 59 067006 A | 4/1984 |
| JP | 62/205009 | 3/1986 |
| JP | 649482 | 6/1994 |
| JP | 0649482 B | 6/1994 |
| JP | 1999033084 A | 2/1999 |
| JP | 2010531350 | 9/2010 |
| RU | 2082436 C | 6/1997 |
| RU | 2233854 C | 8/2004 |
| SU | 862816 A | 9/1981 |
| SU | 925673 A | 5/1982 |
| SU | 1632629 A | 3/1991 |
| WO | WO 91/12881 | 9/1991 |
| WO | WO 92/04920 A | 4/1992 |
| WO | WO 92/06679 | 4/1992 |
| WO | WO 93/13758 A1 | 7/1993 |
| WO | WO 94/06416 | 3/1994 |
| WO | WO 95/09044 A1 | 4/1995 |
| WO | WO 97/38679 A2 | 10/1997 |
| WO | WO 98/32426 A1 | 7/1998 |
| WO | WO 99/17771 | 4/1999 |
| WO | WO 99/44580 A1 | 9/1999 |
| WO | WO 00/04281 | 1/2000 |
| WO | WO 02/47607 | 6/2002 |
| WO | WO 03/059327 A1 | 7/2003 |
| WO | WO 03/061399 A1 | 7/2003 |
| WO | WO 03/101431 A1 | 12/2003 |
| WO | WO 04/000197 A2 | 12/2003 |
| WO | WO 2004/046296 A1 | 6/2004 |
| WO | WO 2004/100857 A2 | 11/2004 |
| WO | WO 2004/110413 A | 12/2004 |
| WO | WO 2006/018074 A1 | 2/2006 |
| WO | WO 2006/127618 | 11/2006 |
| WO | WO 2007/042153 A1 | 4/2007 |
| WO | 2007/104574 A2 | 9/2007 |
| WO | WO 2007/125545 A2 | 11/2007 |
| WO | WO 2007/141328 | 12/2007 |
| WO | WO 2008/005318 A2 | 1/2008 |
| WO | WO 2008/015221 A2 | 2/2008 |
| WO | WO 2009/022670 A | 2/2009 |
| WO | WO 2009/032655 | 3/2009 |
| WO | WO 2009/037319 A2 | 3/2009 |
| WO | WO 2009/080022 A1 | 7/2009 |
| WO | WO 2010/058218 A1 | 5/2010 |
| WO | WO 2012/039788 A1 | 3/2012 |
| ZA | 8704899 | 3/1988 |

OTHER PUBLICATIONS

Int'l Search Report for Application No. PCT/US2008/74375, dated Nov. 17, 2008.
Int'l Search Report for Application No. PCT/US2010/049909 dated Dec. 3, 2010.
Int'l Search Report for Application No. PCT/US2010/049915 dated Mar. 25, 2011.
Int'l Search Report for Application No. PCT/US2010/049925 dated Dec. 8, 2010.
Int'l Search Report for Application No. PCT/US2010/049931 dated Jan. 7, 2011.
Int'l Search Report for Application No. PCT/US2010/049933 dated Feb. 15, 2011.
Int'l Search Report for Application No. PCT/US2010/049964 dated Dec. 30, 2010.
Int'l Search Report for Application No. PCT/US2010/049971 dated Jan. 7, 2011.
Int'l Search Report for Application No. PCT/US2011/029155 dated Jun. 28, 2011.
Int'l Search Report for Application No. PCT/US2011/029158 dated Jun. 28, 2011.
Int'l Search Report for Application No. PCT/US2011/029161 dated Jun. 28, 2011.
Int'l Search Report for Application No. PCT/US2010/049974 dated Mar. 5, 2013.
U.S. Appl. No. 13/718,357, filed Dec. 18, 2012—Pending.
U.S. Appl. No. 13/803,527, filed Mar. 14, 2013.
U.S. Appl. No. 13/804,109, filed Mar. 14, 2013.
U.S. Appl. No. 13/804,410, filed Mar. 14, 2013.
Jones, P. L. et al, "Dielectric Drying", Drying Technology, 14(5), 1996, p. 1063-1098.
Guo, et al., Temperature and Moisture Dependent Dielectric Properties of Legume Flour Associated with Dielectric Heating, LWT Food Science and Technology 43, 2010, p. 193-201.
Katsuki, et al., Novel Energy-Saving Materials for Microwave Heating, Chem Mater. 2008, 20, p. 4803-4807.
Radio-Frequency Heating of Plastics, TechCommentary, vol. 4, No. 2, 1987, p. 1-4.
Jones, P. L., High Frequency Dielectric Heating in Paper Making, Drying Technology, 4(2), 1986, p. 217-244.

(56) References Cited

OTHER PUBLICATIONS

What is R.F. Heat Sealing?, Dielectric Sealing Service, Inc., 2007, p. 1-6.
Broadband RF Survey Instruments, ETS•LINDGREN Haladay EMF Measurement, 2002, p. 1-2.
Lamp IR Infrared Heaters: Infrared Lamps for Controlled Concentrated Heating, Research Inc., p. 1-20., Sep. 20, 2010.
Callebaut, Power Quality & Utilisation Guide, Section 7: Energy Efficiency, Mar. 2007, www.leonardo-energy.org, p. 1-9.
Shukla, et al., Mouth Dissolving Tablets I: An Overview of Formulation Technology, Sci Pharm 2009, 76: p. 309-326.
Lieberman, Herbert A. et al., "Pharmaceutical Dosage Forms—Tablets", vol. 2, $2^{nd}$ Ed. pp. 213-217; 327-329, Marcel Dekker, Inc., 1990, New York and Basel.
Lachman, Leon et al., "The Theory and Practice of Industrial Pharmacy", $3^{rd}$ Ed., Chapter 11, pp. 293-345,Lea & Febiger, 1986, Philadelphia.
McConville, J. et al., "Erosion characteristics of an erodible tablet incorporated in a time-delayed capsule device," Drug Development and Industrial Pharmacy, vol. 31, No. 1, 2005, pp. 79-89, XP008108019.
USP 23 (1995) 1216, Tablet Friability, p. 1981.
USP 24, 2000 Version, Acetaminophen, pp. 19-20 and Ibuprofen, p. 856 (1999).
USP 30-NF25, Disintegration, pp. 276-277, 2007.
USP 33—U.S. Pharmacopeia, General Chapter 701—Disintegration, 2008.
Orally Disintegrating Tablets, draft Food and Drug Administration Guidance, Apr. 2007.
Heng, Paul Wan Sia, Chem Pharm Bull, 47 (5) 633-638 (1999).
Koral, Tony, Radio Frequency Heating and Post-Baking, Biscuit World, Issue 4, vol. 7, Nov. 2004.
Dielectric Heating with Microwave Energy, Püschner MikrowellenEnergietechnik, pp. 1-4, Jun. 2007.
Amin, Avani F., Emerging Treands in the Development of Orally Disintegrating Tablet Technology, Pharmainfo.net, vol. 4, Issue 1, Jan. 26, 2006; pp. 1-30.
Matthes, R.; "Chapter 49" from website: http://www.ilo.org/safework_bookshelf/english?content&nd=857170571; made available online Oct. 12, 2004.
Google page showing the availability date of web reference U; provided Mar. 15, 2011.
Rambali, B., et al., International Journal of Pharmaceutics 220 (2001), pp. 129-140.
Radio Frequency Company, Microwave, (Feb. 19, 2004), pp. 1-2.
Maltodextrin (Maltrin M580), Apr. 20, 2000, (PFormulate Excipients).
International search report for application PCT/US2015/010647 dated Mar. 18, 2015.
International Search Report mailed Aug. 20, 2013 for corresponding Patent Application No. PCT/US2013/039045.
International Search Report mailed Aug. 21, 2013 for corresponding Patent Application No. PCT/US2013/039061.
International Search Report mailed Jun. 8, 2013 for corresponding Patent Application No. PCT/US2013/039047.
U.S. Appl. No. 11/847,444, filed Aug. 30, 2007, Bunick et al., Pending.
U.S. Appl. No. 12/570,046, filed Sep. 30, 2009, Bunick et al., Pending.
U.S. Appl. No. 60/983,973, filed Oct. 31, 2007, Bunick et al., Expired.
U.S. Appl. No. 12/260,151, filed Oct. 29, 2008, Bunick et al., Abandoned.
U.S. Appl. No. 12/566,078, filed Sep. 24, 2009, Bunick et al., Pending.
U.S. Appl. No. 12/566,096, filed Sep. 24, 2009, Bunick et al., Abandoned.
U.S. Appl. No. 61/245,315, filed Sep. 24, 2009, Sowden et al., Expired.
U.S. Appl. No. 61/255,582, filed Oct. 28, 2009, Sowden et al., Expired.
U.S. Appl. No. 61/314,629, filed Mar. 17, 2010, Kriksunov et al., Expired.
U.S. Appl. No. 61/358,167, filed Jun. 24, 2010, Luber et al., Expired.
U.S. Appl. No. 12/887,544, filed Sep. 22, 2010, Bunick et al., Granted.
U.S. Appl. No. 12/887,552, filed Sep. 22, 2010, Bunick et al., Pending.
U.S. Appl. No. 12/887,560, filed Sep. 22, 2010, Kriksunov et al., Granted.
U.S. Appl. No. 12/887,564, filed Sep. 22, 2010, Luber et al., Pending.
U.S. Appl. No. 12/887,569, filed Sep. 22, 2010, Sowden et al., Granted.
U.S. Appl. No. 12/887,575, filed Sep. 22, 2010, Koll et al., Granted.
U.S. Appl. No. 12/887,582, filed Sep. 22, 2010, Luber et al., Granted.
U.S. Appl. No. 12/887,593, filed Sep. 22, 2010, Hugerth et al., Pending.
U.S. Appl. No. 13/052,316, filed Mar. 21, 2011, Luber et al., Pending.
U.S. Appl. No. 13/052,219, filed Mar. 21, 2011, Sowden et al., Issued.
U.S. Appl. No. 13/052,200, filed Mar. 21, 2011, Luber et al., Pending.
U.S. Appl. No. 13/246,884, filed Sep. 28, 2011, Sowdent et al., Pending.
U.S. Appl. No. 13/718,357, filed Dec. 18, 2012, Koll et al., Granted.
U.S. Appl. No. 14/455,126, filed Aug. 8, 2014, Luber et al., Pending.
U.S. Appl. No. 61/640,910, filed May 1, 2012, Chen et al., Expired.
U.S. Appl. No. 61/704,767, filed Sep. 2012, Chen et al., Expired.
U.S. Appl. No. 61/704,773, filed Sep. 24, 2012, Anderson et al., Expired.
U.S. Appl. No. 61/704,780, filed Sep. 24, 2012, Stuhl et al., Expired.
U.S. Appl. No. 13/803,527, filed Mar. 14, 2013, Chen et al., Pending.
U.S. Appl. No. 13/804,109, filed Mar. 14, 2013, Sowden et al., Pending.
U.S. Appl. No. 13/804,229, filed Mar. 14, 2013, Anderson et al., Pending.
U.S. Appl. No. 13/804,410, filed Mar. 14, 2013, Stuhl et al., Pending.
U.S. Appl. No. 61/925,713, filed Jan. 10, 2014, Szymezak etal., Pending.
Heng, P., et al., Melt Processes for Oral Solid Dosage Forms, Encyclopedia of Pharmaceutical Technology, vol. 4, Jan. 2, 2007, pp. 2257-2261.
International Search Report mailed Aug. 20, 2031 for Application No. PCT/US2013/039045.
International Search Report mailed Aug. 21, 2013 for Application No. PCT/US2013/039061.
European Search Report mailed Aug. 1, 2013 for Application No. E{08798740.
International Search Report mailed Nov. 7, 2013 for corresponding Application No. PCT/US2013/039040.
European Search Report mailed Aug. 1, 2013 for Application No. EP08798740.

\* cited by examiner

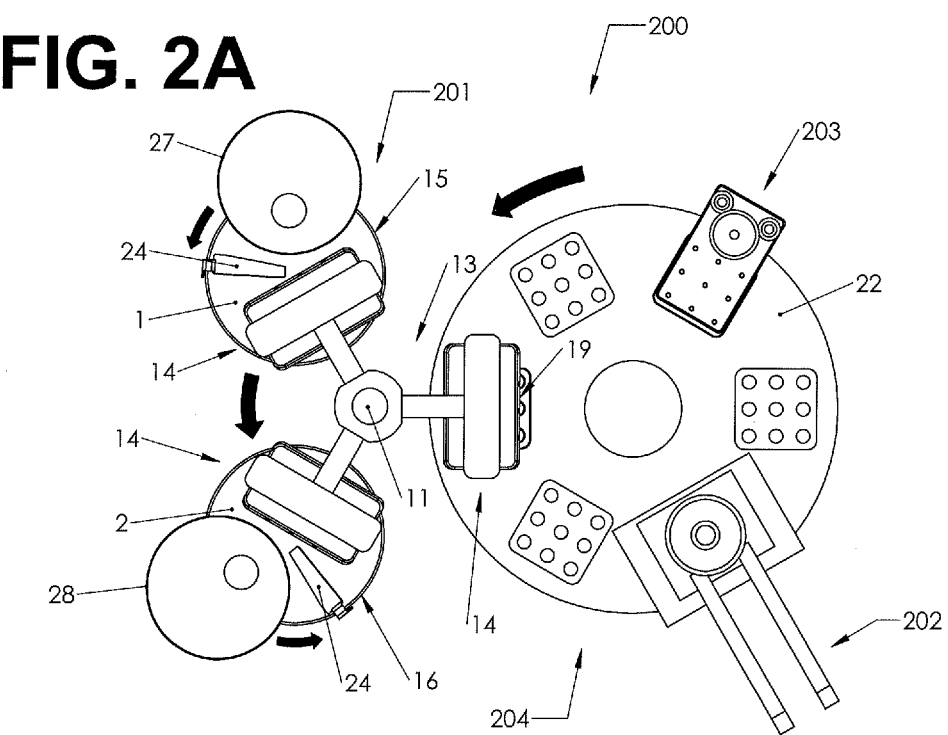
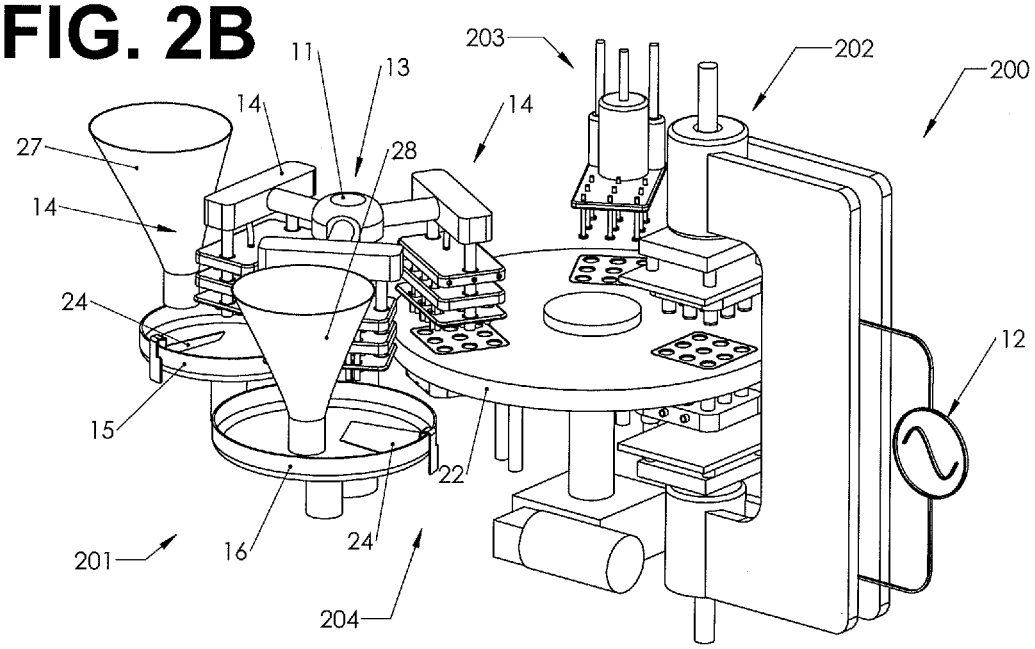

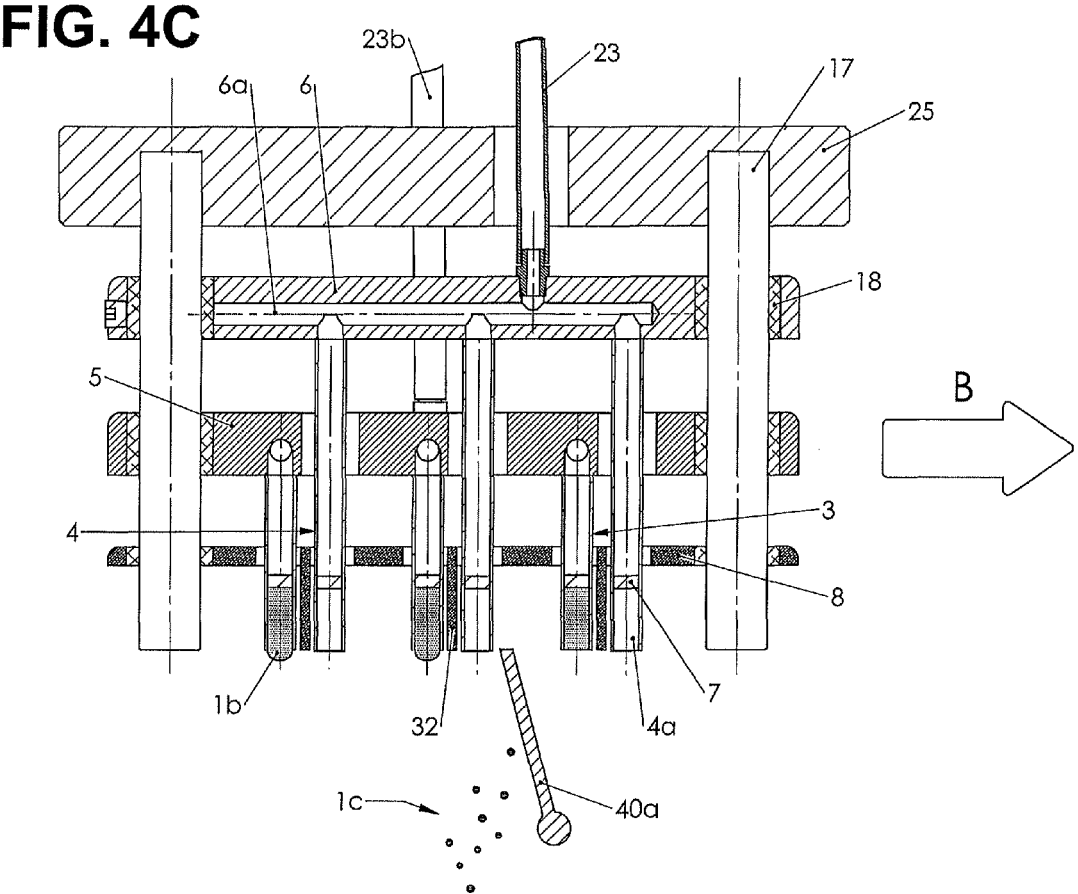

METHOD OF MANUFACTURING SOLID DOSAGE FORM

CROSS REFERENCE TO RELATED APPLICATIONS

This application claims priority of the benefits of U.S. Provisional Application Ser. No. 61/640,910, filed May 1, 2012, and U.S. Provisional Application Ser. No. 61/704,773, filed Sep. 24, 2012. The complete disclosure of the aforementioned related U.S. patent application is hereby incorporated by reference for all purposes.

BACKGROUND OF THE INVENTION

Pharmaceutical tablets and other confectionery compressed tablet forms are very common and widely accepted delivery vehicles for pharmaceutical actives or powders. They provide a convenient means to compress a relatively large volume of low density powders into a smaller compact format that is easily handled, swallowed, or chewed. Various shapes, sizes, and configurations are common in the marketplace. The vast majority of these tablet forms are manufactured from dry blends of compressible powders or granulations that are then fed into rotary tablet compression machines (e.g., such as those commercially available from Fette America Inc., Rockaway, N.J. or Manesty Machines LTD, Liverpool, UK). These tablet compression machines accurately dose a predefined amount of powder into a die cavity. The powder is then compressed using punches which impinge upon the powder and compact it within the die cavity. The final step in the operation is to eject the finished tablet form from the die cavity completing the manufacturing sequence. Most tablet constructions made from this process are simple single component forms; however these machines can sometimes be modified to produce more complex multi-layer tablets by adding multiple feeding and compression stations. Multi-layer tablets produced by this means are procedure in a sequential and stepwise fashion whereby layers or sections are built up layer upon layer. Each layer requires an additional dosing assembly punches and an additional compression assembly. Since these machines have a relatively massive construction due to the very high compaction forces required to get formulations to compact properly (machines capable of producing up to 20,000 pounds force are quite common) multi-layer machines can become very expensive and hard to maintain. An additional drawback to producing tablets in this fashion is the limitations of the layered geometry. Regions of a tablet with an orientation that is perpendicular to the tablet ejection direction are extremely hard to produce and would require more elaborate and complex modifications.

A further drawback to the layer upon sequence of tablet manufacturing is specific to the production of orally disintegrating tablets. These tablets require a low density and highly porous tablet construction whereby saliva of the mouth quickly penetrates the tablet to break down the particle bonds to create a fast dissolve effect. The layer upon layer approach requires that a first layer of powdered material is first filled into a die cavity with the surface of the die cavity being scraped to establish the required volume of fill. This first fill layer is then compressed with a punch to a controlled depth of penetration into the die cavity. This depth of penetration must be precisely controlled and the powder must be uniformly compacted to create a controlled volume for the second fill of powder material. The next step of the operation is to fill this newly created volume with a second powder. This powder is then scraped flush with top surface of the die cavity and the final step is to compact the second layer upon the first layer a second time with a punch which presses upon both layers of the tablet. This double compaction smashes the tiny air pockets between particles causing a detrimental effect to the porous structure that is desired for the orally disintegrating tablet. In pharmaceutical manufacturing it is not possible to skip this double compression step because a dense uniform first layer is a prerequisite to achieving accurate dosing of the powdered medicament of the second layer. Accurate dosing of drugs by pharmaceutical manufacturers is critical to maintaining the health and safety of patients.

SUMMARY OF THE INVENTION

In one aspect, the present invention features a method of manufacturing a solid dosage form, the method including the steps of: (a) measuring an amount of a first powder blend within a dosing nozzle, wherein the first powder blend includes a pharmaceutically active agent; (b) discharging the measured amount of a first powder blend from the dosing nozzle into a forming cavity within a die block, the forming cavity having an inner wall, a first opening at the surface of one side of the die block, and a second opening at the surface on the opposite side of the die block; (c) moving a first forming tool into the forming cavity through the first opening of the forming cavity such that the first powder blend is formed into the shape of the dosage form within the forming cavity between the inner wall, the first forming tool and a second forming tool within or adjacent to the cavity; (d) applying RF energy between a first electrode and a second electrode such that the energy heats the first powder blend within the forming cavity to form the dosage form; and (e) removing the dosage form from the forming cavity.

In another aspect, the present invention features a method of manufacturing a solid dosage form, the method including the steps of: (a) measuring an amount of a first powder blend within a first dosing nozzle wherein the first powder blend includes a pharmaceutically active agent; (b) discharging the measured amount of the first powder blend from the first dosing nozzle into a forming cavity within a die block, the forming cavity having an inner wall, a first opening at the surface of one side of the die block, and a second opening at the surface on the opposite side of the die block; (c) measuring an amount of a second powder blend within a second dosing nozzle; (d) discharging the measured amount of a second powder blend from the dosing nozzle into the forming cavity; (e) moving a first forming tool into the forming cavity through the first opening of the forming cavity such that the first powder blend and the second powder blend are formed into the shape of the dosage form within the forming cavity between the inner wall, the first forming tool and a second forming tool within or adjacent to the cavity; (f) applying RF energy between a first electrode and a second electrode such that the energy heats the first powder blend within the forming cavity to form the dosage form; and (g) removing the dosage form from the forming cavity.

In yet another aspect, the present invention features a method of manufacturing a solid dosage form, the method including the steps of: (a) measuring an amount of a first powder blend within a first dosing nozzle wherein the first powder blend includes a pharmaceutically active agent; (b) discharging the measured amount of the first powder blend from the first dosing nozzle into a forming cavity within a die block, the forming cavity having an inner wall, a first opening at the surface of one side of the die block, and a second opening at the surface on the opposite side of the die block, wherein the forming chamber further includes a movable divider adapted to form the first chamber and a second chamber within the forming cavity and the first powder blend is discharged into the first chamber; (c) measuring an amount of a second powder blend within a second dosing nozzle; (d) discharging the measured amount of the second powder blend from the dosing nozzle into the second chamber; (e) removing the movable divider from within the forming cavity such that the first powder blend contacts the second powder blend within the forming cavity; (f) moving a first forming tool into the forming cavity through the first opening of the forming cavity such that the first powder blend and the second powder blend are formed into the shape of the dosage form within the forming cavity between the inner wall, the first forming tool and a second forming tool within or adjacent to the cavity; (g) applying RF energy between the first electrode and the second electrode such that the energy heats the first powder blend within the forming cavity to form the dosage form; and (h) removing the dosage form from the forming cavity.

Other features and advantages of the present invention will be apparent from the detailed description of the invention and from the claims.

BRIEF DESCRIPTION OF THE FIGURES

FIG. 2A is an overhead view of multi-component tablet machine 200.

FIG. 2B is a perspective view of multi-component tablet machine 200.

FIG. 4B-4C is a perspective view of dosing module 14 moving from the first powder tray 15 to second powder tray 16.

DETAILED DESCRIPTION OF THE INVENTION

Figure 1A:
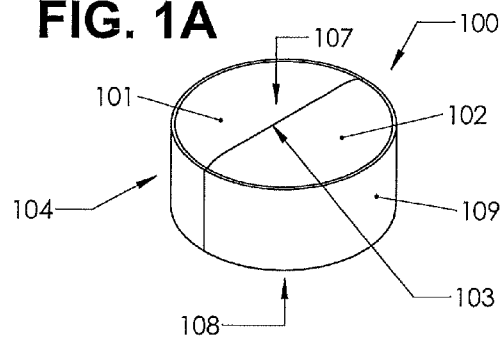
FIGS. 1A-G are perspective views of multi-region tablets.

It is believed that one skilled in the art can, based upon the description herein, utilize the present invention to its fullest extent. The following specific embodiments can be construed as merely illustrative, and not limitative of the remainder of the disclosure in any way whatsoever.

Unless defined otherwise, all technical and scientific terms used herein have the same meaning as commonly understood by one of ordinary skill in the art to which the invention belongs. Also, all publications, patent applications, patents, and other references mentioned herein are incorporated by reference. As used herein, all percentages are by weight unless otherwise specified.

As discussed above, in one aspect, the present invention features the present invention features a method of manufacturing a solid dosage form, the method including the steps of: (a) measuring an amount of a first powder blend within a dosing nozzle, wherein the first powder blend includes a pharmaceutically active agent; (b) discharging the measured amount of a first powder blend from the dosing nozzle into a forming cavity within a die block, the forming cavity having an inner wall, a first opening at the surface of one side of the die block, and a second opening at the surface on the opposite side of the die block; (c) moving a first forming tool into the forming cavity through the first opening of the forming cavity such that the first powder blend is formed into the shape of the dosage form within the forming cavity between the inner wall, the first forming tool and a second forming tool within or adjacent to the cavity; (d) applying RF energy between a first electrode and a second electrode such that the energy heats the first powder blend within the forming cavity to form the dosage form; and (e) removing the dosage form from the forming cavity.

While the specific embodiments herein focus on tablets, other dosage forms such as lozenges and chewing gums can also be made by such machine and process.

Powder Blend

In one embodiment, the tablet is manufactured by applying energy to a powder blend containing at least one pharmaceutically active agent (as discussed herein) and, optionally, at least one first material (as discussed herein), at least one second material (as discussed herein), at least one meltable binder (as discussed herein), and/or other suitable excipients.

In one embodiment, the powder blend has a density of less than about 0.5 g/cc, such as less than about 0.4 g/cc, such as less than about 0.3 g/cc. In one embodiment, the powder blend is substantially free of liquid material (e.g., less than 1%, such as less than 0.5%, such as less than 0.01%, such as 0%).

In one embodiment, the powder blend contains at least one first material and at least one second material. In one embodiment, the at least one pharmaceutically active agent are contained within particles, such as polymer-coated particles. In one embodiment, the total amount of such particles, the at least one first material, and the at least one second material include at least 90%, by weight, of the powder blend/tablet, such as at least 95%, such as at least 98%, by weight of the powder blend/tablet.

In one embodiment, the powder blend/tablet includes at least 60%, by weight, of the at least one first material and the at least one second material, such as at least 75%, such as at least 90%. In one embodiment, the ratio of the at least one first material to the at least one second material is from about 20:80 to about 70:30, such as from about 25:75 to about 60:40, such as about 35:65 to about 45:55.

Examples of suitable excipients include, but are not limited to, lubricants, glidants, sweeteners, flavor and aroma agents, antioxidants, preservatives, texture enhancers, colorants, and mixtures thereof. One or more of the above ingredients may be present on the same particle of the powder blend.

Suitable lubricants include, but are not limited to, long chain fatty acids and their salts, such as magnesium stearate and stearic acid, talc, glycerides waxes, and mixtures thereof.

Suitable glidants include, but are not limited to, colloidal silicon dioxide.

Examples of sweeteners for the present inventions include, but are not limited to high intensity sweeteners such as synthetic or natural sugars; artificial sweeteners such as saccharin, sodium saccharin, aspartame, acesulfame, thaumatin, glycyrrhizin, sucralose, dihydrochalcone, alitame, miraculin, monellin, and stevside.

Examples of flavors and aromatics include, but are not limited to, essential oils including distillations, solvent extractions, or cold expressions of chopped flowers, leaves, peel or pulped whole fruit containing mixtures of alcohols, esters, aldehydes and lactones; essences including either diluted solutions of essential oils, or mixtures of synthetic chemicals blended to match the natural flavor of the fruit (e.g., strawberry, raspberry and black currant); artificial and natural flavors of brews and liquors, e.g., cognac, whisky, rum, gin, sherry, port, and wine; tobacco, coffee, tea, cocoa, and mint; fruit juices including expelled juice from washed, scrubbed fruits such as lemon, orange, and lime; spear mint, pepper mint, wintergreen, cinnamon, cacoe/cocoa, vanilla, liquorice, menthol, eucalyptus, aniseeds nuts (e.g., peanuts, coconuts, hazelnuts, chestnuts, walnuts, colanuts), almonds, raisins; and powder, flour, or vegetable material parts including tobacco plant parts, e.g., genus *Nicotiana*, in amounts not contributing significantly to the level of nicotine, and ginger.

Examples of antioxidants include, but are not limited to, tocopherols, ascorbic acid, sodium pyrosulfite, butylhydroxytoluene, butylated hydroxyanisole, edetic acid, and edetate salts, and mixtures thereof.

Examples of preservatives include, but are not limited to, citric acid, tartaric acid, lactic acid, malic acid, acetic acid, benzoic acid, and sorbic acid, and mixtures thereof.

Examples of texture enhancers include, but are not limited to, pectin, polyethylene oxide, and carrageenan, and mixtures thereof. In one embodiment, texture enhancers are used at levels of from about 0.1% to about 10% percent by weight.

In one embodiment of the invention, the powder blend has an average particle size of less than 500 microns, such as from about 50 microns to about 500 microns, such as from about 50 microns and 300 microns. Particles in this size range are particularly useful for direct compacting processes.

In one embodiment, the powder blend is substantially free of polyethylene glycols, hydrated cellulose polymers, gums (such as xanthan gum and carrageenans), and gelatins. As used herein, what is meant by "substantially free" is less than 5%, such as less than 1%, such as less than 0.1%, such as completely free (e.g., 0%). Such a composition is advantageous for maintaining an immediate release dissolution profile, minimizing processing and material costs, and providing for optimal physical and chemical stability of the tablet.

In one embodiment, the powder blend/tablet is substantially free of directly compressible water insoluble fillers. Water insoluble fillers include but are not limited to microcrystalline cellulose, directly compressible microcrystalline cellulose, celluloses, water insoluble celluloses, starch, cornstarch and modified starches. As described in this embodiment, substantially free is less than 2 percent, e.g. less than 1 percent or none.

In one embodiment, the powder blend is substantially free of super disintegrants. Super disintegrants include cross carmellose sodium, sodium starch glycolate, and cross-linked povidone. A composition substantially free of super-disintegrants is advantageous for enhancing mouth-feel and tablet stability due to reduced water absorbance.

In one embodiment, at least 90%, by weight, of the tablet is comprised of material having a melting point greater than 60° C., such as at least 70° C., such as at least 80° C.

First Material

The powder blend/tablet of the present invention includes at least one first material which is a dielectric water-containing material (i) including from about 1 to about 5 percent, by weight, of bound water, such as from about 1.5 to about 3.2 percent, by weight, of bound water, such as from about 1.7 to about 3 percent, by weight of bound water and (ii) has a dielectric loss, when measured at a density of between 0.15 and 0.5 g/cc, of from about 0.05 to about 0.7, such as from about 0.1 to about 0.5, such as 0.25 to about 0.5.

In one embodiment, the first material is a starch. Examples of such starches include, but are not limited to, hydrolyzed starches such as maltodextrin and corn syrup solids. Such starches may be sourced from a variety of vegetable sources, such as grain, legume, and tuber, and examples include, but are not limited to, starches sourced from corn, wheat, rice, pea, bean, tapioca and potato.

In one embodiment, the first material when added to the powder blend has a bulk density of less than about 0.4 g/cc, such as less than about 0.3 g/cc, such as less than 0.2 g/cc.

In one embodiment, the average particle size of the first material is less than 500 microns, such as less than 150 microns.

The first material(s) may be present at level of at least about 15 percent, by weight, of the tablet, such as at least about 20 percent, such as from about 20 percent to about 45 percent of the powder blend/tablet, such as from about 20 percent to about 42 of the powder blend/tablet, such as from about 20 percent to about 40 of the powder blend/tablet.

Second Material

In one embodiment, the powder blend/tablet of the present invention includes at least one second material (i) having a water solubility from about 20 to about 400 g per 100 g of water at 25° C., (ii) having a dielectric loss, when measured at a density between 0.5 and 1.1 g/cc, of less than about 0.05, such as less than about 0.01, such as less than 0.005, such as about 0. In one embodiment, the second material is crystalline at 25° C.

In one embodiment, the second material is a sugar or an alcohol or hydrate thereof. Examples of sugars include, but are not limited to, monosaccharides and disaccharides such as sucrose, fructose, maltose, dextrose, and lactose, and alcohols and hydrates thereof.

Examples of sugar alcohols include, but are not limited to, erythritol, isomalt, mannitol, maltitol, lactitol, sorbitol, and xylitol.

The second material(s) may be present at level of about 18 percent to about 72 percent of the powder blend/tablet, such as from about 20 percent to about 64 percent of the powder blend/tablet, such as from about 39 percent to about 56 percent of the powder blend/tablet.

Meltable Binder

In one embodiment, the powder blend/tablet of the present invention includes at least one meltable binder. In one embodiment, the meltable binder has a melting point of from about 40° C. to about 140° C., such as from about 55° C. to about 100° C. The softening or melting of the meltable binder(s) results in the sintering of the tablet shape through the binding of the softened or melted binder with the pharmaceutically active agent and/or other ingredients within the compacted powder blend.

In one embodiment, the meltable binder is a RF-meltable binder. What is meant by an RF-meltable binder is a solid binder that can be softened or melted upon exposure to RF energy. The RF-meltable binder typically is polar and has the capability to re-harden or resolidify upon cooling.

In one embodiment, the meltable binder is not a RF-meltable binder. In such embodiment, the powder blend contains an excipient that heats upon exposure to RF energy (e.g., a polar excipient), such that the resulting heat from is able to soften or melt the meltable binder. Examples of such excipients include, but are not limited to, polar liquids such as water and glycerin; powdered metals and metal salts such as powdered iron, sodium chloride, aluminum hydroxide, and magnesium hydroxide; stearic acid; and sodium stearate.

Examples of suitable meltable binders include: fats such as cocoa butter, hydrogenated vegetable oil such as palm kernel oil, cottonseed oil, sunflower oil, and soybean oil; mono, di, and triglycerides; phospholipids; cetyl alcohol; waxes such as Carnauba wax, spermaceti wax, beeswax, candelilla wax, shellac wax, microcrystalline wax, and paraffin wax; water soluble polymers such as polyethylene glycol, polycaprolactone, GlycoWax-932, lauroyl macrogol-32 glycerides, and stearoyl macrogol-32 glycerides; polyethylene oxides; and sucrose esters.

In one embodiment, the meltable binder is a RF-meltable binder, and the RF-meltable binder is a polyethylene glycol (PEG), such as PEG-4000. A particularly preferred RF-meltable binder is PEG having at least 95% by weight of the PEG particles less than 100 microns (as measured by conventional means such as light or laser scattering or sieve analysis) and a molecular weight between 3000 and 8000 Daltons.

The meltable binder(s) may be present at level of about 0.01 percent to about 70 percent of the powder blend/tablet, such as from about 1 percent to about 50 percent, such as from about 10 percent to about 30 percent of the powder blend/tablet.

Carbohydrate

In one embodiment, the powder blend/tablet contains at least one carbohydrate in addition to any first material, second material, or meltable binder that is also a carbohydrate. In one embodiment, the powder blend/tablet contains both a meltable binder and a carbohydrate. The carbohydrate can contribute to the dissolvability and mouth feel of the tablet, aid in distributing the other ingredients across a broader surface area, and diluting and cushioning the pharmaceutically active agent. Examples of carbohydrates include, but are not limited to, water-soluble compressible carbohydrates such as sugars (e.g., dextrose, sucrose, maltose, isomalt, and lactose), starches (e.g., corn starch), sugar-alcohols (e.g., mannitol, sorbitol, maltitol, erythritol, lactitol, and xylitol), and starch hydrolysates (e.g., dextrins, and maltodextrins).

The carbohydrate(s) may be present at level of about 5 percent to about 95 percent of the powder blend/tablet, such as from about 20 percent to about 90 percent or from about 40 percent to about 80 percent of the powder blend/tablet. When a meltable binder is contained within the powder blend, the particle size of the of carbohydrate can influence the level of meltable binder used, wherein a higher particle size of carbohydrate provides a lower surface area and subsequently requires a lower level of meltable binder. In one embodiment, wherein the carbohydrate(s) is greater than 50% by weight of the powder blend and the mean particle size of the carbohydrate(s) is greater than 100 microns, then the meltable binder is from about 10 to about 30 percent by weight of the powder blend/tablet.

Pharmaceutically Active Agent

The powder blend/tablet of the present invention includes at least one pharmaceutically active agent containing particles. What is meant by a "pharmaceutically active agent" is an agent (e.g., a compound) that is permitted or approved by the U.S. Food and Drug Administration, European Medicines Agency, or any successor entity thereof, for the oral treatment of a condition or disease. Suitable pharmaceutically active agents include, but are not limited to, analgesics, anti-inflammatory agents, antipyretics, antihistamines, antibiotics (e.g., antibacterial, antiviral, and antifungal agents), antidepressants, antidiabetic agents, antispasmodics, appetite suppressants, bronchodilators, cardiovascular treating agents (e.g., statins), central nervous system treating agents, cough suppressants, decongestants, diuretics, expectorants, gastrointestinal treating agents, anesthetics, mucolytics, muscle relaxants, osteoporosis treating agents, stimulants, nicotine, and sedatives.

Examples of suitable gastrointestinal treating agents include, but are not limited to: antacids such as aluminum-containing pharmaceutically active agents (e.g., aluminum carbonate, aluminum hydroxide, dihydroxyaluminum sodium carbonate, and aluminum phosphate), bicarbonate-containing pharmaceutically active agents, bismuth-containing pharmaceutically active agents (e.g., bismuth aluminate, bismuth carbonate, bismuth subcarbonate, bismuth subgallate, and bismuth subnitrate), calcium-containing pharmaceutically active agents (e.g., calcium carbonate), glycine, magnesium-containing pharmaceutically active agents (e.g., magaldrate, magnesium aluminosilicates, magnesium carbonate, magnesium glycinate, magnesium hydroxide, magnesium oxide, and magnesium trisilicate), phosphate-containing pharmaceutically active agents (e.g., aluminum phosphate and calcium phosphate), potassium-containing pharmaceutically active agents (e.g., potassium bicarbonate), sodium-containing pharmaceutically active agents (e.g., sodium bicarbonate), and silicates; laxatives such as stool softeners (e.g., docusate) and stimulant laxatives (e.g., bisacodyl); H2 receptor antagonists, such as famotidine, ranitidine, cimetadine, and nizatidine; proton pump inhibitors such as omeprazole, dextansoprazole, esomeprazole, pantoprazole, rabeprazole, and lansoprazole; gastrointestinal cytoprotectives, such as sucraflate and misoprostol; gastrointestinal prokinetics such as prucalopride; antibiotics for H. pylori, such as clarithromycin, amoxicillin, tetracycline, and metronidazole; antidiarrheals, such as bismuth subsalicylate, kaolin, diphenoxylate, and loperamide; glycopyrrolate; analgesics, such as mesalamine; antiemetics such as ondansetron, cyclizine, diphenyhydroamine, dimenhydrinate, meclizine, promethazine, and hydroxyzine; probiotic bacteria including but not limited to lactobacilli; lactase; racecadotril; and antiflatulents such as polydimethylsiloxanes (e.g., dimethicone and simethicone, including those disclosed in U.S. Pat. Nos. 4,906,478, 5,275,822, and 6,103,260); isomers thereof; and pharmaceutically acceptable salts and prodrugs (e.g., esters) thereof.

Examples of suitable analgesics, anti-inflammatories, and antipyretics include, but are not limited to, non-steroidal anti-inflammatory drugs (NSAIDs) such as propionic acid derivatives (e.g., ibuprofen, naproxen, ketoprofen, flurbiprofen, fenbufen, fenoprofen, indoprofen, ketoprofen, fluprofen, pirprofen, carprofen, oxaprozin, pranoprofen, and suprofen) and COX inhibitors such as celecoxib; acetaminophen; acetyl salicylic acid; acetic acid derivatives such as indomethacin, diclofenac, sulindac, and tolmetin; fenamic acid derivatives such as mefanamic acid, meclofenamic acid, and flufenamic acid; biphenylcarbodylic acid derivatives such as diflunisal and flufenisal; and oxicams such as piroxicam, sudoxicam, isoxicam, and meloxicam; isomers thereof; and pharmaceutically acceptable salts and prodrugs thereof.

Examples of antihistamines and decongestants, include, but are not limited to, bromopheniramine, chlorcyclizine, dexbrompheniramine, bromhexane, phenindamine, pheniramine, pyrilamine, thonzylamine, pripolidine, ephedrine, phenylephrine, pseudoephedrine, phenylpropanolamine, chlorpheniramine, dextromethorphan, diphenhydramine, doxylamine, astemizole, terfenadine, fexofenadine, naphazoline, oxymetazoline, montelukast, propylhexadrine, triprolidine, clemastine, acrivastine, promethazine, oxomemazine, mequitazine, buclizine, bromhexine, ketotifen, terfenadine, ebastine, oxatamide, xylomeazoline, loratadine, desloratadine, and cetirizine; isomers thereof; and pharmaceutically acceptable salts and esters thereof.

Examples of cough suppressants and expectorants include, but are not limited to, diphenhydramine, dextromethorphan, noscapine, clophedianol, menthol, benzonatate, ethylmorphine, codeine, acetylcysteine, carbocisteine, ambroxol, belladona alkaloids, sobrenol, guaiacol, and guaifenesin; isomers thereof; and pharmaceutically acceptable salts and prodrugs thereof.

Examples of muscle relaxants include, but are not limited to, cyclobenzaprine and chlorzoxazone metaxalone, orphenadrine, and methocarbamol; isomers thereof; and pharmaceutically acceptable salts and prodrugs thereof.

Examples of stimulants include, but are not limited to, caffeine.

Examples of sedatives include, but are not limited to sleep aids such as antihistamines (e.g., diphenhydramine), eszopiclone, and zolpidem, and pharmaceutically acceptable salts and prodrugs thereof.

Examples of appetite suppressants include, but are not limited to, phenylpropanolamine, phentermine, and diethylcathinone, and pharmaceutically acceptable salts and prodrugs thereof.

Examples of anesthetics (e.g., for the treatment of sore throat) include, but are not limited to dyclonine, benzocaine, and pectin and pharmaceutically acceptable salts and prodrugs thereof.

Examples of suitable statins include but are not limited to atorvastin, rosuvastatin, fluvastatin, lovastatin, simvustatin, atorvastatin, pravastatin and pharmaceutically acceptable salts and prodrugs thereof.

In one embodiment, the pharmaceutically active agent contained within the tablet is selected from phenylephrine, dextromethorphan, pseudoephedrine, acetaminophen, cetirizine, aspirin, nicotine, ranitidine, ibuprofen, ketoprofen, loperamide, famotidine, calcium carbonate, simethicone, chlorpheniramine, methocarbomal, chlophedianol, ascorbic acid, pectin, dyclonine, benzocaine and menthol, and pharmaceutically acceptable salts and prodrugs thereof.

As discussed above, the pharmaceutically active agents of the present invention may also be present in the form of pharmaceutically acceptable salts, such as acidic/anionic or basic/cationic salts. Pharmaceutically acceptable acidic/anionic salts include, and are not limited to acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate, pantothenate, phosphate/diphospate, polygalacturonate, salicylate, stearate, subacetate, succinate, sulfate, tannate, tartrate, teoclate, tosylate and triethiodide. Pharmaceutically acceptable basic/cationic salts include, and are not limited to aluminum, benzathine, calcium, chloroprocaine, choline, diethanolamine, ethylenediamine, lithium, magnesium, meglumine, potassium, procaine, sodium and zinc.

As discussed above, the pharmaceutically active agents of the present invention may also be present in the form of prodrugs of the pharmaceutically active agents. In general, such prodrugs will be functional derivatives of the pharmaceutically active agent, which are readily convertible in vivo into the required pharmaceutically active agent. Conventional procedures for the selection and preparation of suitable prodrug derivatives are described, for example, in "Design of Prodrugs", ed. H. Bundgaard, Elsevier, 1985. In addition to salts, the invention provides the esters, amides, and other protected or derivatized forms of the described compounds.

Where the pharmaceutically active agents according to this invention have at least one chiral center, they may accordingly exist as enantiomers. Where the pharmaceutically active agents possess two or more chiral centers, they may additionally exist as diastereomers. It is to be understood that all such isomers and mixtures thereof are encompassed within the scope of the present invention. Furthermore, some of the crystalline forms for the pharmaceutically active agents may exist as polymorphs and as such are intended to be included in the present invention. In addition, some of the pharmaceutically active agents may form solvates with water (e.g., hydrates) or common organic solvents, and such solvates are also intended to be encompassed within the scope of this invention.

In one embodiment, the pharmaceutically active agent or agents are present in the tablet in a therapeutically effective amount, which is an amount that produces the desired therapeutic response upon oral administration and can be readily determined by one skilled in the art. In determining such amounts, the particular pharmaceutically active agent being administered, the bioavailability characteristics of the pharmaceutically active agent, the dose regime, the age and weight of the patient, and other factors must be considered, as known in the art.

The pharmaceutically active agent may be present in various forms. For example, the pharmaceutically active agent may be dispersed at the molecular level, e.g. melted, within the tablet, or may be in the form of particles, which in turn may be coated or uncoated. If the pharmaceutically active agent is in form of particles, the particles (whether coated or uncoated) typically have an average particle size of from about 1 to about 500 microns. In one embodiment, such particles are crystals having an average particle size of from about 1 to about 300 microns.

The pharmaceutically active agent may be present in pure crystal form or in a granulated form prior to the addition of the taste masking coating. Granulation techniques may be used to improve the flow characteristics or particle size of the pharmaceutically active agents to make it more suitable for compaction or subsequent coating. Suitable binders for making the granulation include but are not limited to starch, polyvinylpyrrolidone, polymethacrylates, hydroxypropylmethylcellulose, and hydroxypropylcellulose. The particles including pharmaceutically active agent(s) may be made by cogranulating the pharmaceutically active agent(s) with suitable substrate particles via any of the granulation methods known in the art. Examples of such granulation method include, but are not limited to, high sheer wet granulation and fluid bed granulation such as rotary fluid bed granulation.

If the pharmaceutically active agent has an objectionable taste, the pharmaceutically active agent may be coated with a taste masking coating, as known in the art. Examples of suitable taste masking coatings are described in U.S. Pat. Nos. 4,851,226, 5,075,114, and 5,489,436. Commercially available taste masked pharmaceutically active agents may also be employed. For example, acetaminophen particles, which are encapsulated with ethylcellulose or other polymers by a coacervation process, may be used in the present invention. Coacervation-encapsulated acetaminophen may be purchased commercially from Eurand America, Inc. (Vandalia, Ohio).

In one embodiment, the tablet incorporates modified release coated particles (e.g., particles containing at least one pharmaceutically active agent that convey modified release properties of such agent). As used herein, "modified release" shall apply to the altered release or dissolution of the active agent in a dissolution medium, such as gastrointestinal fluids. Types of modified release include, but are not limited to, sustained release or delayed release. In general, modified release tablets are formulated to make the active agents(s) available over an extended period of time after ingestion, which thereby allows for a reduction in dosing frequency compared to the dosing of the same active agent(s) in a conventional tablet. Modified release tablets also permit the use of active agent combinations wherein the duration of one pharmaceutically active agent may differ from the duration of another pharmaceutically active agent. In one embodiment the tablet contains one pharmaceutically active agent that is released in an immediate release manner and an additional active agent or a second portion of the same active agent as the first that is modified release.

Examples of swellable, erodible hydrophilic materials for use as a release modifying excipient for use in the modified release coating include water swellable cellulose derivatives, polyalkylene glycols, thermoplastic polyalkylene oxides, acrylic polymers, hydrocolloids, clays, and gelling starches. Examples of water swellable cellulose derivatives include sodium carboxymethylcellulose, cross-linked hydroxypropylcellulose, hydroxypropyl cellulose (HPC), hydroxypropylmethylcellulose (HPMC), hydroxyisopropylcellulose, hydroxybutylcellulose, hydroxyphenylcellulose, hydroxyethylcellulose (HEC), hydroxypentylcellulose, hydroxypropylethylcellulose, hydroxypropylbutylcellulose, and hydroxypropylethylcellulose. Examples of polyalkylene glycols include polyethylene glycol. Examples of suitable thermoplastic polyalkylene oxides include poly (ethylene oxide). Examples of acrylic polymers include potassium methacrylatedivinylbenzene copolymer, polymethylmethacrylate, and high-molecular weight cross-linked acrylic acid homopolymers and copolymers.

Suitable pH-dependent polymers for use as release-modifying excipients for use in the modified release coating include: enteric cellulose derivatives such as hydroxypropyl methylcellulose phthalate, hydroxypropyl methylcellulose acetate succinate, and cellulose acetate phthalate; natural resins such as shellac and zein; enteric acetate derivatives such as polyvinylacetate phthalate, cellulose acetate phthalate, and acetaldehyde dimethylcellulose acetate; and enteric acrylate derivatives such as for example polymethacrylate-based polymers such as poly(methacrylic acid, methyl methacrylate) 1:2 (available from Rohm Pharma GmbH under the tradename EUDRAGIT S) and poly(methacrylic acid, methyl methacrylate) 1:1 (available from Rohm Pharma GmbH under the tradename EUDRAGIT L).

In one embodiment the pharmaceutically active agent is coated with a combination of a water insoluble film forming polymer (such as but not limited to cellulose acetate or ethylcellulose) and a water soluble polymer (such as but not limited to povidone, polymethacrylic co-polymers such as those sold under the tradename Eudragit E-100 from Rohm America, and hydroxypropylcellulose). In this embodiment, the ratio of water insoluble film forming polymer to water soluble polymer is from about 50 to about 95 percent of water insoluble polymer and from about 5 to about 50 percent of water soluble polymer, and the weight percent of the coating by weight of the coated taste-masked particle is from about 5 percent to about 40 percent. In one embodiment, the coating which is used in the coated particle of the pharmaceutically active agent is substantially free of a material (such as polyethylene glycol) which melts below 85° C., in order to prevent damage to the integrity of the coating during the RF heating step.

In one embodiment, one or more pharmaceutically active agents or a portion of the pharmaceutically active agent may be bound to an ion exchange resin for the purposes of taste-masking the pharmaceutically active agent or delivering the active in a modified release manner.

In one embodiment, the pharmaceutically active agent is capable of dissolution upon contact with a fluid such as water, stomach acid, intestinal fluid or the like. In one embodiment, the dissolution characteristics of the pharmaceutically active agent within the tablet meets USP specifications for immediate release tablets including the pharmaceutically active agent. For example, for acetaminophen tablets, USP 24 specifies that in pH 5.8 phosphate buffer, using USP apparatus 2 (paddles) at 50 rpm, at least 80% of the acetaminophen contained in the tablet is released there from within 30 minutes after dosing, and for ibuprofen tablets, USP 24 specifies that in pH 7.2 phosphate buffer, using USP apparatus 2 (paddles) at 50 rpm, at least 80% of the ibuprofen contained in the tablet is released there from within 60 minutes after dosing. See USP 24, 2000 Version, 19-20 and 856 (1999). In another embodiment, the dissolution characteristics of the pharmaceutically active agent are modified: e.g. controlled, sustained, extended, retarded, prolonged, delayed and the like.

In one embodiment, the pharmaceutically active agent(s) are comprised within polymer-coated particles (e.g., taste-masked and/or sustained release coated particles).

In one embodiment, the particles including the pharmaceutically active agents(s) may be present at level from about 10% to about 40%, by weight of the tablet/powder blend, such as 15% to about 35%, by weight of the tablet/powder blend, such as 20% to about 30%, by weight of the tablet/powder blend. In one embodiment, the particles including the pharmaceutically active agents(s) may be present at level of at least about 15%, by weight, of the powder blend/tablet, such as at least about 20%, by weight, of the powder blend/tablet.

Multi-Region Tablet

The multi-region tablets contain two or more regions that have distinctly different physical compositions such as shown in FIGS. 1A-1G. In one embodiment, each region of the tablet has a unique function or sensory attribute. An example of this is a tablet constructed with a component region having a fast dissolve orally disintegrating composition and an adjacent component region having a formulation that has a slow dissolve lozenge like composition. Alternatively a tablet can be constructed with separate component regions containing distinctly different pharmaceutical actives such as a first component containing a pain relieving medicament such as acetaminophen or ibuprofen and a second component region containing upper respiratory medicament such as decongestants such as phenylephrine or pseudoephedrine or antihistamines such as diphenhydramine or cetirizine. Similarly, a tablet can be manufactured with a composition having an immediate release medicament combined with a component having a controlled release medicament. In an alternate embodiment, tablets can also be constructed with multiple component regions of similar composition and functionality, but having differing aesthetic attributes such as color, taste, or texture.

In one embodiment, the second region has a higher density than the first region. In one embodiment, the density of the second region is at least 10% greater than the density of the first region. In one embodiment, the second region is a lozenge. In the embodiment wherein the second region is a lozenge, the region (e.g., the powder blend used to create the region) contains at least one amorphous carbohydrate polymer. What is meant by an "amorphous carbohydrate polymer" is a molecule having a plurality of carbohydrate monomers wherein such molecule has a crystallinity of less than 20%, such as less than 10%, such as less than 5%. Examples of amorphous carbohydrate polymers include, but are not limited to hydrogenated starch hydrosolate, polydextrose, and oligosaccharides. Examples of oligosaccharides include, but are not limited to, fructo-oligosaccharide, galacto-oligosaccharide malto-oligosaccharide, inulin, and isolmalto-oligosaccharide.

In one embodiment, the interface between the regions is along at least one of the major faces of the tablet. In one embodiment, the interface is along two major faces of the tablet (e.g., the interface extends through the tablet).

A tablet with two such component regions is shown in FIG. 1A. In this illustration, tablet 100 has a first major face 107, a second major face 108, and a side wall 109. The tablet is composed of first region 101 and adjacent second region 102. The interface 103 separating the regions is a straight line in this tablet configuration. The first region 101 and second region 102 can have a similar appearance which would make the interface 103 indistinguishable from the rest of the tablet. However, in a preferred embodiment of the invention, the first region 101 and second region 102 can have different colors, different textures, and/or different optical properties, such as opaqueness or transparency to create a visually noticeable interface 103.

The novelty of the current invention lies not only in the multi component construction of the tablet, but also in the fact that the component regions of the tablet have interfaces that are parallel to the tablet side walls 104 which are shown in the vertical orientation in FIG. 1A. In compression based tablet manufacturing technologies these walls are linear and parallel in order to facilitate the ejection of the tablet from the cavity which forms the tablet during the manufacturing process. The tablets are slid out of the forming cavity in a linear fashion. Tablets produced by existing technologies such as bi-layer tablets produced on machines manufactured by Korsch America Inc. (South Easton, Mass.) and Fette Compacting America (Rockaway, N.J.) can have multiple regions, however they require a sequential layer upon layer construction with interfaces which are generally perpendicular to the die wall. In one embodiment, the present invention allows for the manufacture of a tablet possessing an interface between two or more regions that is parallel to the die wall.

Figure 1B:
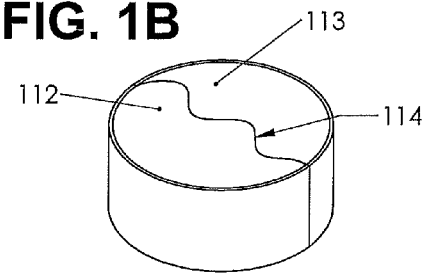
Figure 1C:
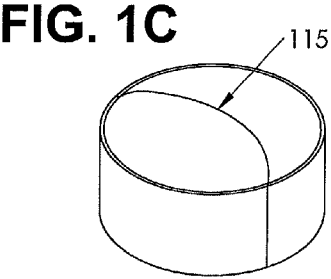
Figure 1D:
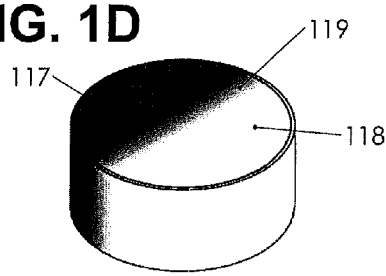
Figure 1E:
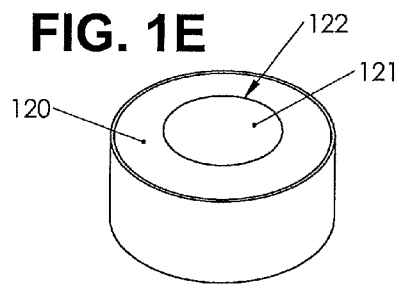
Figure 1F:
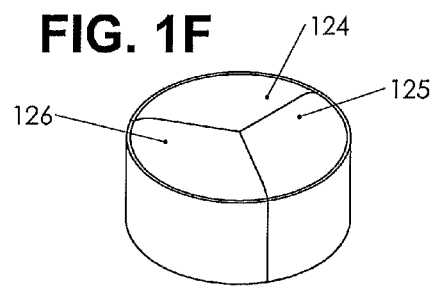
Figure 1G:
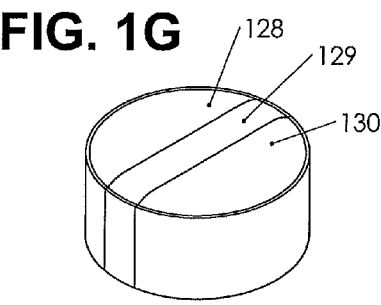

Another novel aspect of the current invention is that the region interfaces can be produced to have curvilinear as well as linear geometries that can be configured to achieve unique visual or functional effects. This is illustrated in FIG. 1B where the interface 114 between first region 112 and second region 113 is a wavy, curvilinear line. FIG. 1C illustrates a tablet with an arc shaped interface 115. FIG. 1D illustrates a tablet having a first region 117 and a second region 118 that has a blended interface region 119. In this embodiment, the interface is not a crisp line, but rather a region of intermingled powder formulation offering a unique aesthetic. FIG. 1E represents a further variation where a tablet where a first region 122 is fully surrounded by a second region 121 with a circular interface 122, thus forming a bulls eye geometry. The tablets describes so far have all had two regions, however, three or more regions can also be used. FIG. 1F shows just such a tablet with first region 124, second region 125, and third region 126. FIG. 1G illustrates a three component tablet where first region 128 and second region 130 are separated by a barrier region 129. With this tablet contraction, incompatible or reactive drug products can be separated from each other with a barrier component.

The embodiments disclosed all offer unique tablet aesthetics which can be used as a tablet identifier to help distinguish one medicament from another. The more unique and distinctive the tablet, the less likely it is to mistakenly ingest the wrong drug.

Manufacturing Method for Multi-Region Tablets

In one aspect, the present invention features a machine capable of producing multi-region tablet wherein the interface between the first region and the second region is along a major face of the tablet. One embodiment of such a machine is depicted in FIGS. 2A and 2B. FIG. 2A illustrates a plan view of an embodiment of this invention, and FIG. 2B illustrates a three dimensional view of this embodiment. Multi-region tablet machine 200 is composed of four major assemblies; namely powder dosing station 201, rotary table assembly 204, forming station 202, and tablet ejection station 203.

Figure 8A:
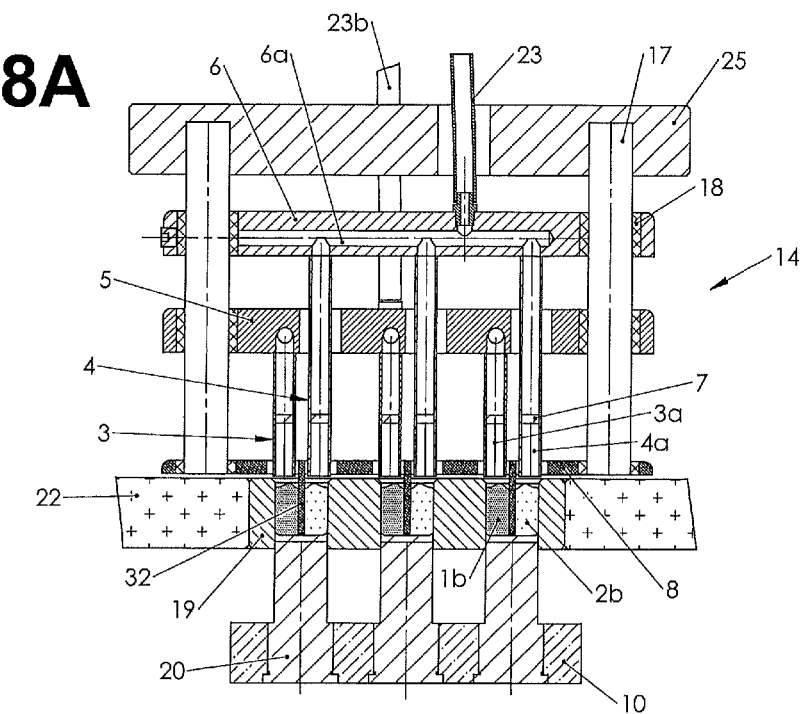
FIGS. 8A-8B are cross sections of dosing module 14 over die block 19.

The powder dosing station 201 is designed to accurately dose multiple powder blends. It is comprised of a first powder blend tray 15 which contains powder blend bed 1 and second powder blend tray 16 which contains powder blend bed 2. Powder blends are fed into the first powder blend tray 15 and second powder blend tray 16 through feed hoppers 27 and 28, respectively. The dosing head assembly 13 is positioned over the powder blend beds 1 and 2 as well as over the rotary table assembly 204. In a preferred embodiment, the dosing head assembly 13 is comprised of three identical dosing modules 14 arrayed radially from a central hub 11. In this embodiment, the rotary dose head assembly sequentially indexes first over powder blend bed 1 to obtain a volume of powder blend from powder blend bed 1. It then indexes over powder blend bed 2 to obtain a volume of powder blend from powder blend bed 2. It then indexes to discharge the two powder blend volumes 1b and 2b into die block 19 on dial plate 22 (as shown in FIG. 8A), which indexes between the powder dosing station 201, forming station 202, and tablet ejection station 203. Although two powder blend volumes are illustrated here, the dosing of three or more separate powder blend volumes could be performed with additional powder blend beds and, optionally, additional dose head assemblies.

In one embodiment, the powder blend beds 1 and 2 are fluffed to help maintain a uniform density and to prevent densification of the powder bed. In one embodiment powder blend trays 15 and 16 rotate while angled blending blade 24 remains stationary, causing powder blend beds 1 and 2 to move up and over the angled blending blade 24. The subsequent lifting and dropping of the powder blend over the trailing edge of the blending blade 24 causes the powder particles to separate and un-clump as they free fall back to the powder blend bed. The angle of blending blade 24 is controlled to achieve varying drop distances thereby achieving the desired fluffing action. Since the powder blend beds 1 and 2 are circular and since the tangential velocity at any point on the powder blend beds 1 and 2 varies according to its radius, the blade can have a geometry that tapers along its access to account for velocity variations along the radius of the beds. A twisting geometry can also be incorporated into the blending blade 24 to control the lift distance and duration at various points along the radius of the powder blend beds. In another embodiment (not shown), a series of angled blending blades can be placed at various locations within the powder blend bed in an orientation that is perpendicular to the bed. These blades are arranged at various angles to move powder blend from the outer radius of the powder blend bed to the inner radius or vise versa. This mixing effect is also useful in dealing with the tangential velocity effect just described. In another embodiment, powder blend beds 1 and 2 remain stationary, and a rotating arm (not shown) within first powder blend trays 15 and 16 mixes powder blend beds 1 and 2.

Figure 3A:
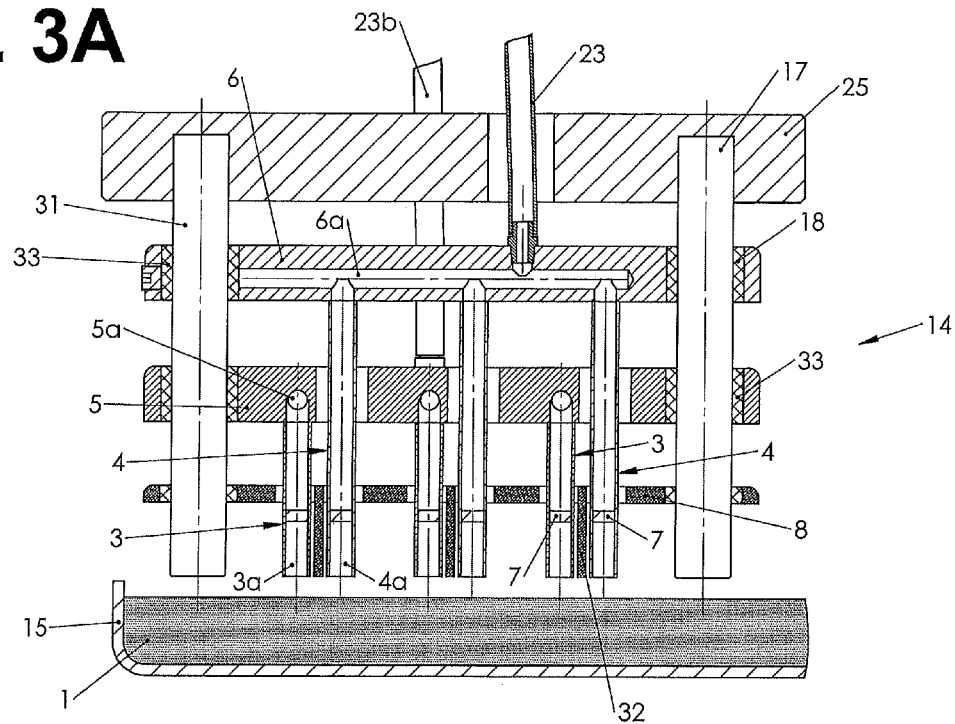
FIGS. 3A-3B are cross sections of dosing module 14 over first powder tray 15.

FIG. 3A shows a cross section through one of the dosing modules 14. In this view, the dosing module 14 is positioned over the first powder blend tray 15, ready to begin a first step in the dosing sequence. The dosing module 14 is comprised of a plurality of dosing nozzles 3 and 4, which have a hollow tube shape. Within each nozzle is a filter 7 which have their position within the tube being adjustable so as to set the desired dose volume of nozzle cavities 3a and 4a. Each nozzle is connected to flow passageways 5a and 6a, respectively, which allow vacuum to be drawn via vacuum tubes 23b and 23, respectively. The longer dosing nozzles 4 are mounted to manifold plate 6, and the shorter dosing nozzles 3 are mounted to manifold plate 5. Both manifold plate 5 and manifold plate 6 are moveable linearly and are guided, respectively, with bearings 18 and 33 upon shaft 17 and shaft 31, both mounted on support 25 which is attached to hub 11. Separating the dosing nozzles are divider plates 32 which are attached to divider mounting plate 8.

Figure 3B:
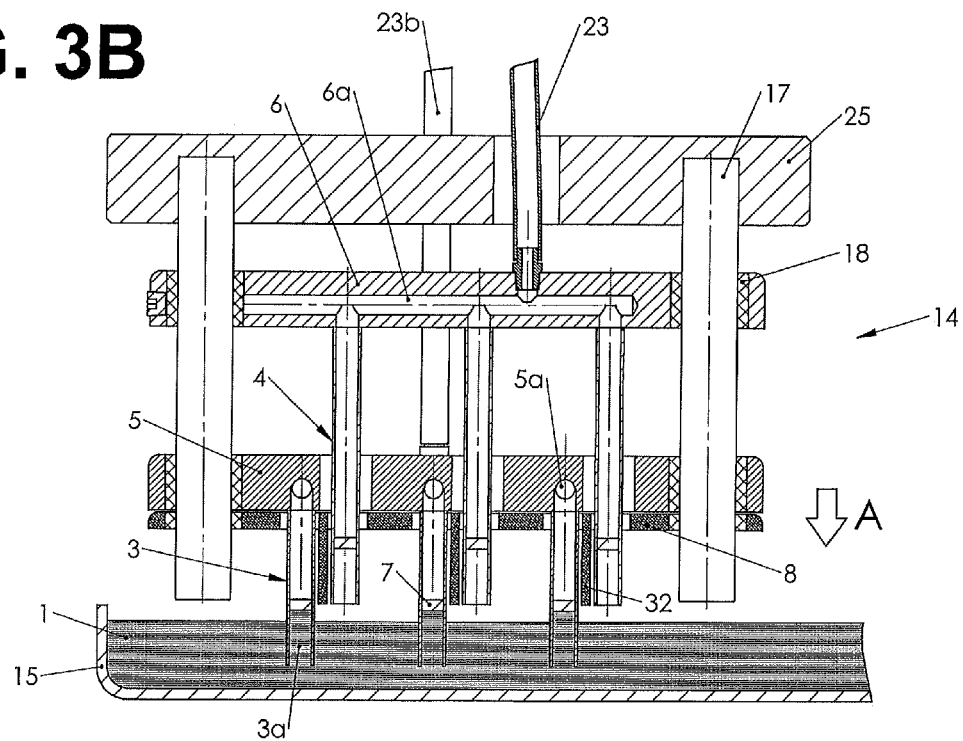
Figure 4A:
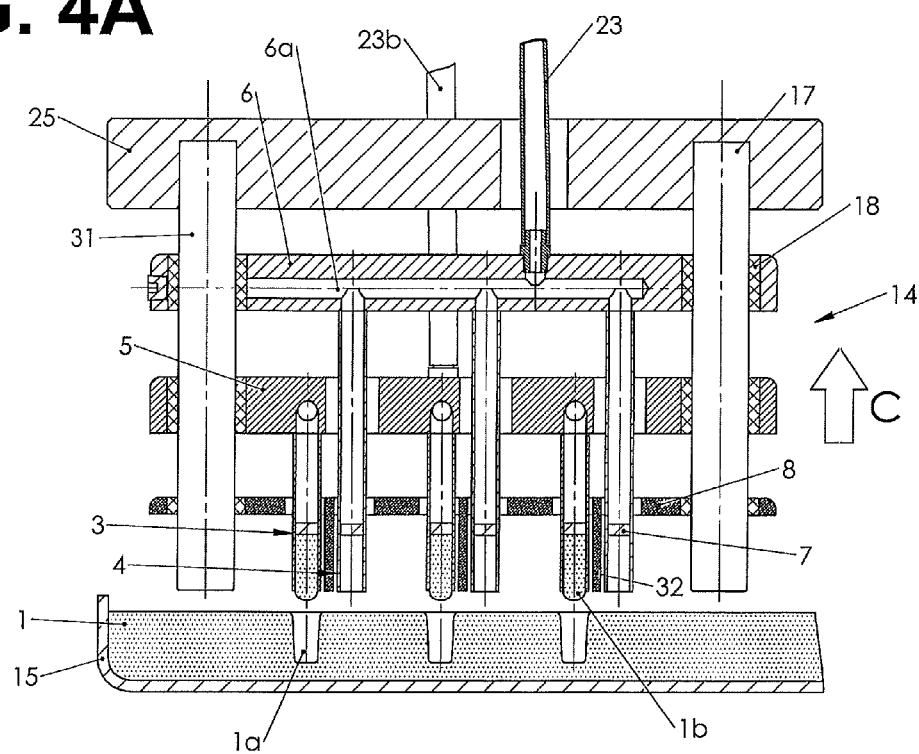
FIG. 4A is a cross section of dosing module 14 over first powder tray 15.

FIG. 3B shows manifold plate 5 and attached dosing nozzles 3 after they have moved down in direction A and penetrated into powder blend bed 1. At this point, the vacuum source which is controlled via an external valve (not shown) is switched on, pulling a vacuum through vacuum tube 23b. Powder blend volume 1b from the powder blend bed 1 is sucked into the nozzle cavity 3a by negative pressure. Filter 7 prevents such powder blend from passing beyond nozzle cavity 3a. The volume of powder blend volume 1b, within nozzle cavity 3a, can be modified by repositioning filter 7 within dosing nozzle 3. Once dosing is complete, the manifold plate 5 is retracted in direction C to the starting position as shown in FIG. 4A. A bulb of excess powder blend 1b that extends beyond nozzle cavity 3a is held in place by such negative pressure. The vacant space 1a left in the powder blend bed 1 as a result of the removal of powder blend volume 1b is also shown. First powder blend tray 15 then receives a fresh charge of first powder blend from feed hopper 27 (as sown in FIG. 2B). The bed is thus regenerated after each fill cycle is complete. Generally this regeneration occurs while the dosing head assembly 14 (shown in FIG. 4B) indexes to its next position.

Figure 4B:
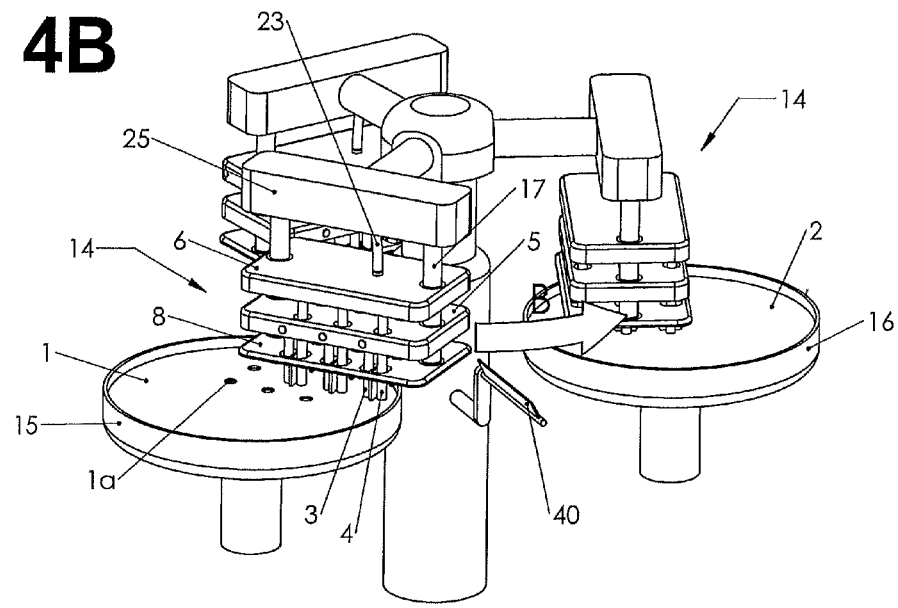

FIG. 4B is a schematic representation of one of the dosing modules 14 moving along direction B from the first powder blend tray 15 to a second powder blend tray 16, which in a preferred embodiment contains a powder blend formulation with a different composition (e.g. color and/or pharmaceutically active agent). An example of this could be where the first powder blend tray 15 contains a colored formulation containing an analgesic and the second powder blend tray 16 contains a formulation of a different color containing a decongestant.

FIG. 4C depicts the removal of excess powder blend volume 1b from nozzle 3 while the dosing head assembly 14 moves from its position over powder blend tray 15 to powder blend tray 16. A scraper bar assembly 40 is positioned in the path of the dosing head assembly. As the dosing head assembly 14 moves horizontally in direction B across the scraper bar assembly 40, the scraper blade 40a, being maintained at an appropriate height, separates the excess powder blend volume 1c from the powder blend volume 1b. The leading edge of scraper blade 40a is sharp and the top face of the scraper blade 40a is maintained flat and parallel to the face of nozzle 3 in order to prevent the excess powder blend volume 1b from being forcibly pushed into the nozzle cavity 3a. Excess powder blend volume 1c is depicted as it falls away from the face of nozzle 3. The excess powder blend is collected in a container (not shown).

Figure 5A:
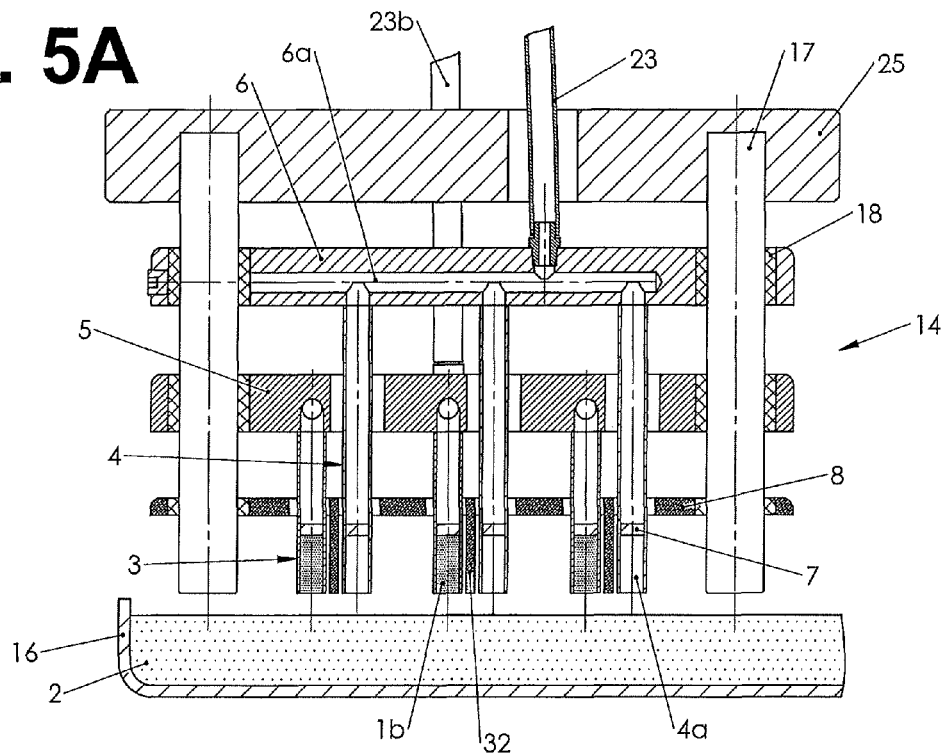
FIGS. 5A-5B are cross sections of dosing module 14 over second powder tray 16.
Figure 5B:
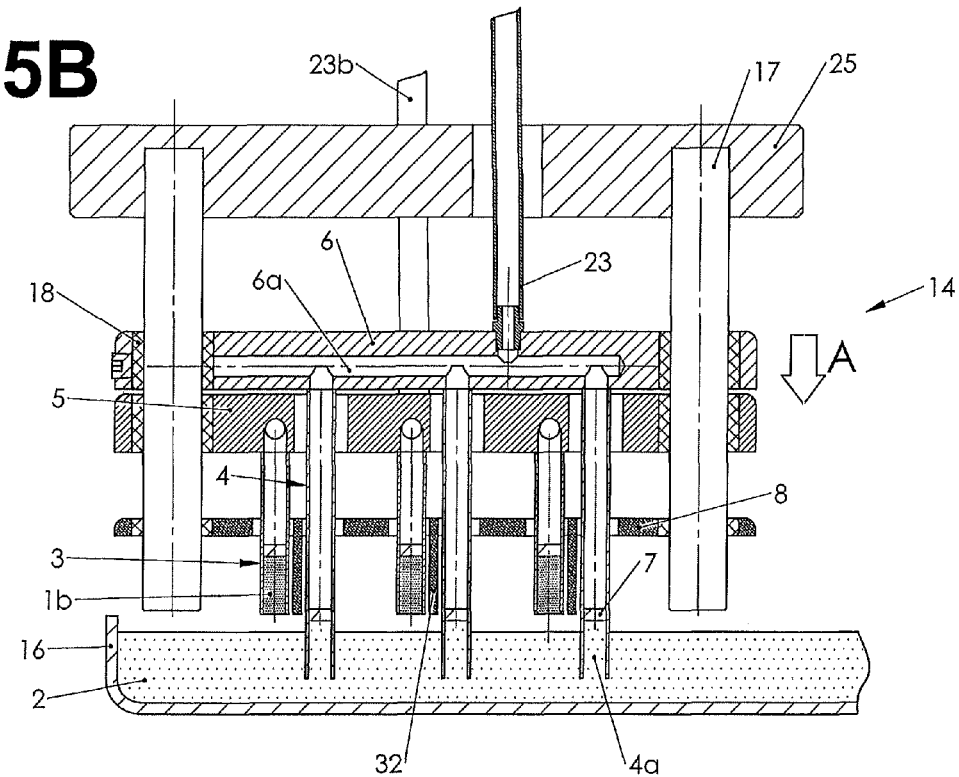
Figure 6A:
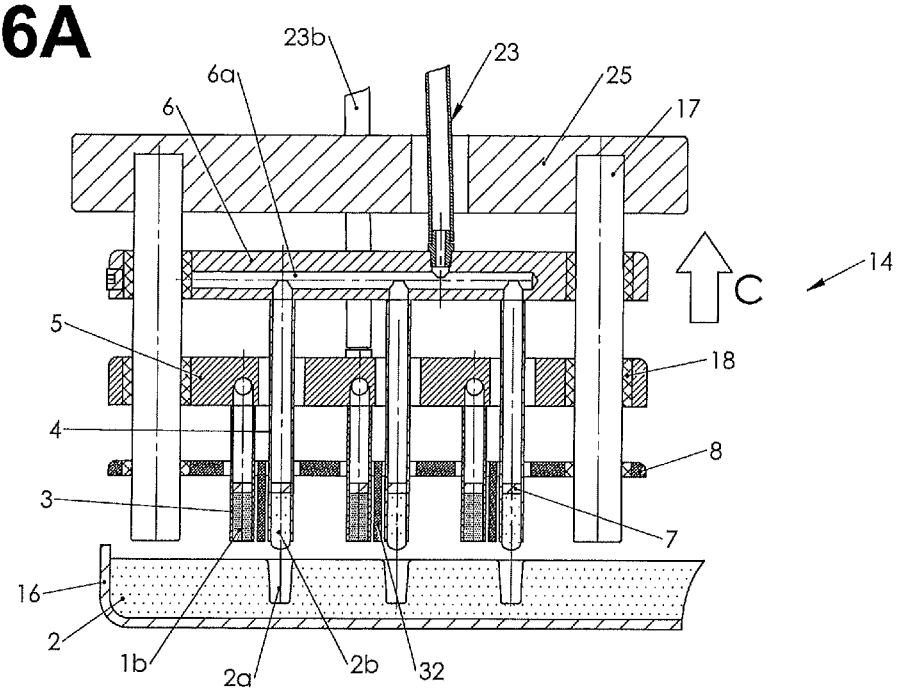
FIG. 6A is a cross section of dosing module 14 over second powder tray 16.

FIG. 5A illustrates a dosing module 14 positioned over rotary tablet tray 16, ready to begin the filling sequence of dosing nozzles 4 with powder blend from powder blend bed 2. The dosing nozzles 3 are shown full of powder blend 1b from the previous filling step shown in FIG. 4A. FIG. 5B shows manifold plate 6 and the dosing nozzles 4 which are attached to it after they have moved down in direction A and penetrated into powder blend bed 2. The vacuum source which is controlled via an external valve (not shown) is switched on and pulls a vacuum through vacuum tube 23. Powder blend from the powder blend bed 2 is sucked into the nozzle cavity 4a by negative pressure. Filter 7 prevents powder blend 2b from passing beyond nozzle cavity 4a. In this embodiment, the fill volume for nozzle cavity 4a is shown to be the same as for nozzle cavity 3a, however, the volume can be different to produce a tablet having regions of different volumes such as the tablet illustrated in FIG. 1C. Once dosing of this nozzle cavity 4a is complete, manifold plate 6 is retracted in direction C to the starting position as shown in FIG. 6A. The vacant space 2a left in the powder blend bed 2 by the filling operation is also shown.

Figure 6B:
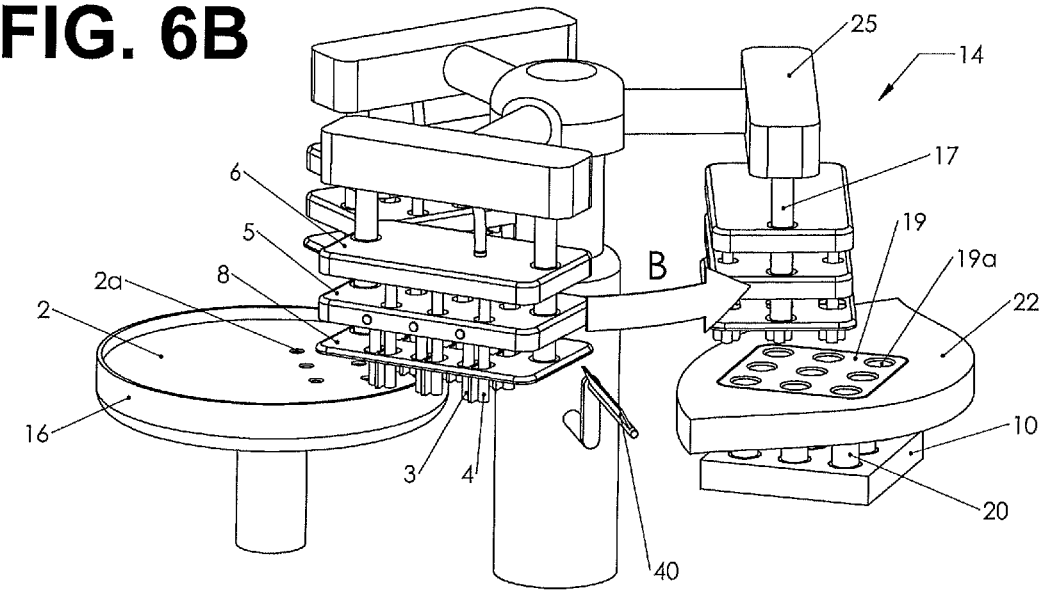
FIG. 6B is a perspective view of dosing module 14 moving from the second powder tray 16 to a position over the die block 19.
Figure 7A:
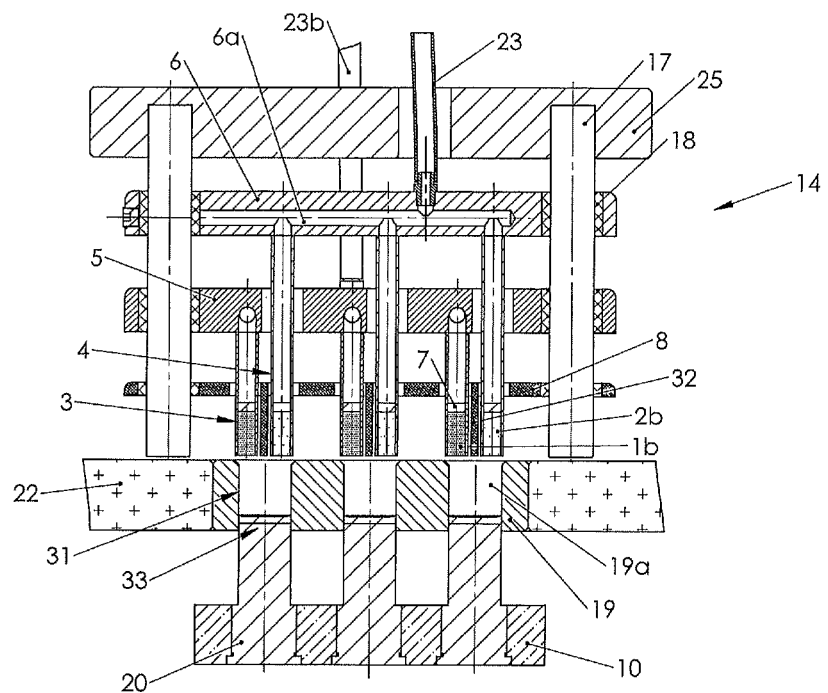
FIGS. 7A and 7C are cross sections of dosing module 14 over die block 19.
Figure 7B:
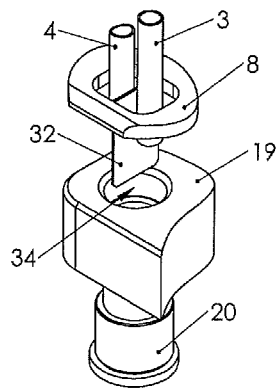
FIG. 7B is a perspective view of a portion of die block 19, forming tool 20, and a portion of the nozzles 3 and 4.
Figure 10:
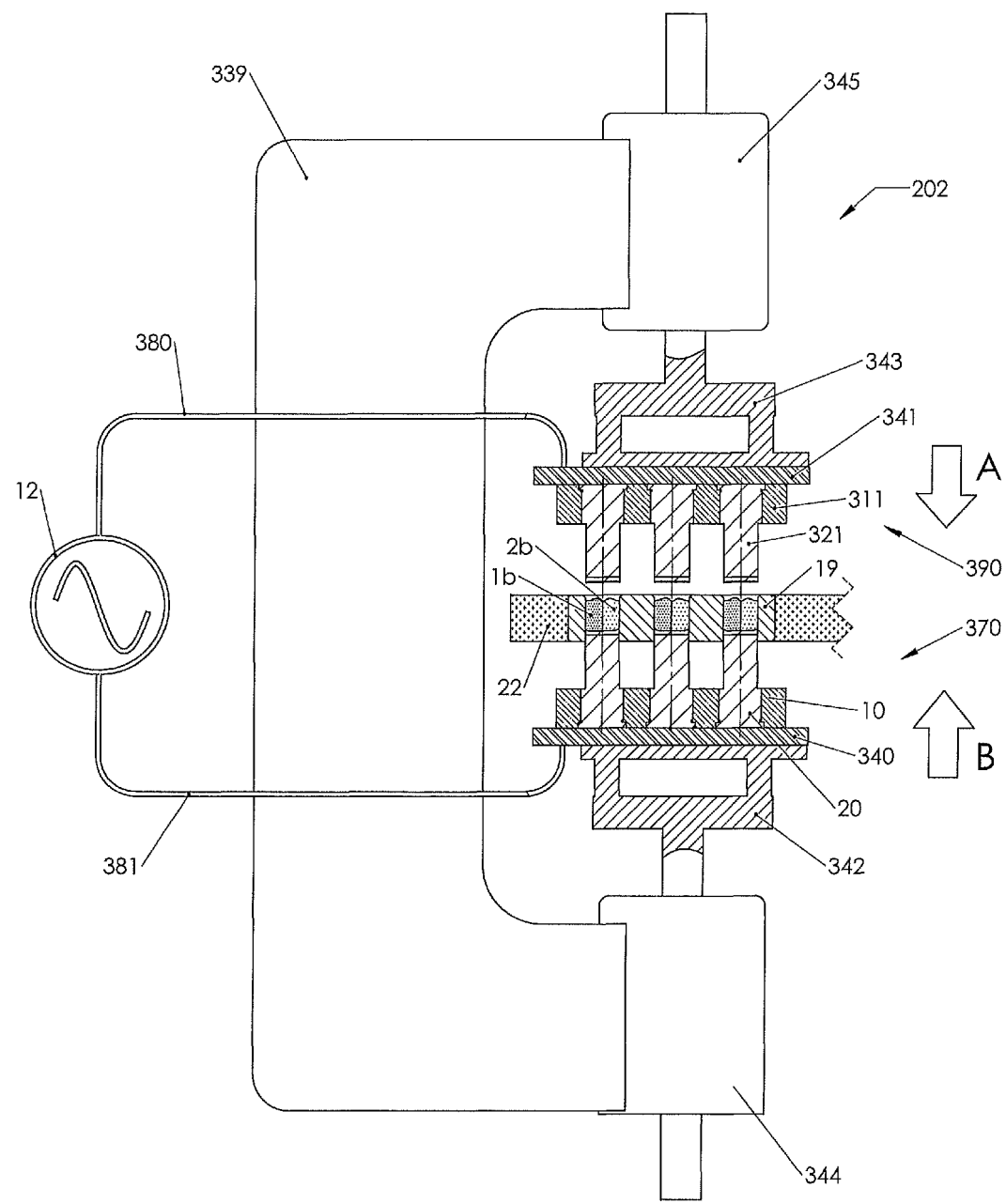
FIG. 10 is a cross section showing movable electrode plate 340 and movable electrode plate 341 in an open position.

FIG. 6B is a schematic representation of one of the dosing modules 14 moving from the second powder blend tray 16 to a position over the die block 19. As dosing module 14 moves, a second scraper bar assembly 40 separates excess powder blend volume from the powder blend volume 2b as discussed above. Die block 19 is mounted with dial plate 22 which is part of the rotary table assembly 204 (as shown in FIG. 2B). The dial plate 22 is synchronized with the dosing head assembly 13 (as shown in FIG. 2B) such that after an indexing motion, dosing module 14 is positioned over the forming cavity 19a, as shown in cross section in FIG. 7A. Each forming cavity 19a has an inner wall 31, and a second opening 33 (for forming tool 20 to enter the forming cavity 19a) and a first opening 34 (for upper forming tool 321 as shown in FIG. 10 to enter the forming cavity 19a). As shown in this illustration, nozzle cavities 3a and 4a (shown empty in FIG. 3A) are now filled with powder blend volumes 1b and 2b, respectively. Lower forming tools 20 have been inserted through second openings 33 in the bottom of die block 19. Forming tools 20 are housed in lower tool holder block 10. FIG. 7B shows a three dimensional view of a portion of the die block 19, forming tool 20, and a portion of the dosing nozzles 3 and 4 which are separated by divider plate 32.

Figure 7C:
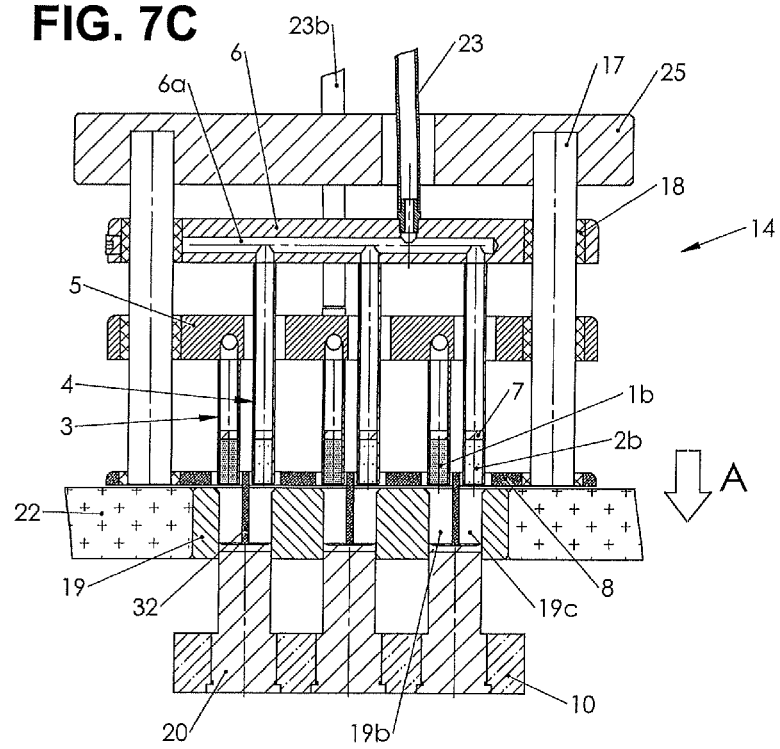

As shown in FIG. 7C, the first step in the sequence of filling the forming cavity 19a entails the insertion of divider plate 32 into the forming cavity 19a. This is accomplished by moving divider mounting plate 8 in direction A down such that movable divider 32 is located within the forming cavity 19a. As shown in the illustration, movable divider 32 creates a barrier within the forming cavity 19a, thereby separating forming cavity 19a it into two die chambers, namely die block chambers 19b and 19c. The movable dividers 32 are constructed of any suitable rigid material such as stainless steel, Delrin®, nylon, or Teflon®. The movable divider has a geometry that contours to the die cavity and lower form tool (e.g., a width that is slightly smaller than the diameter of the die cavity to allow for easy insertion and extraction, such as a clearance of between 0.002 inches to 0.062 inches).

Figure 8B:
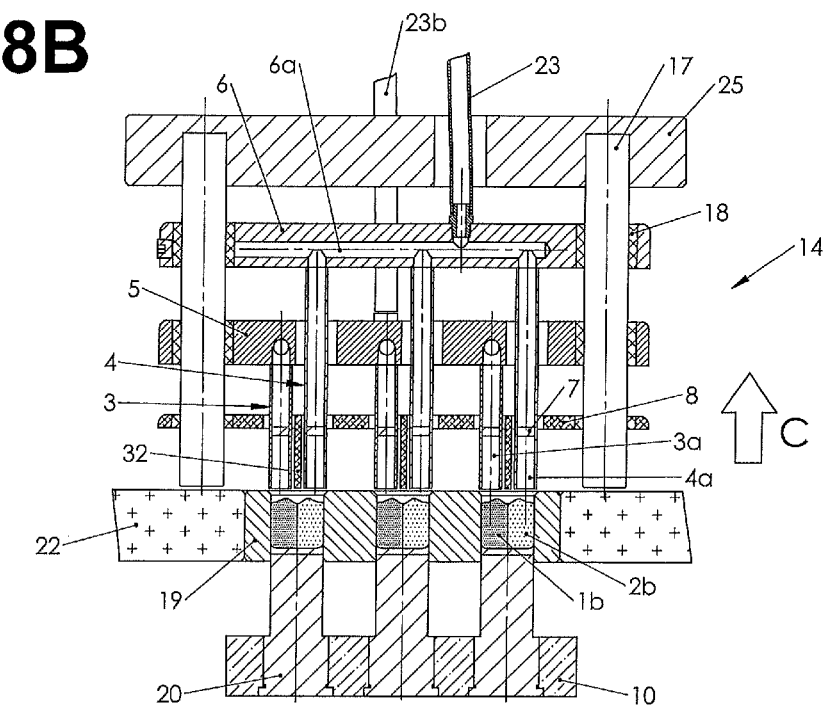

FIG. 8A illustrates the filling sequence of the operation. In this sequence, dosing nozzles 3 and 4 are shown evacuated, with the powder blend 1b and 2b now residing on either side of the movable divider 32, respectively within die block chambers 19b and 19c (as previously shown empty in FIG. 7C). To achieve the full and complete discharge of the powder blend from the nozzles, an external valve switches from a vacuum source to a pressure source, sending positive air pressure through vacuum tubes 23 and 23b. This positive air pressure passes through filters 7 and blows the powder blend volumes 1b and 2b into the die block chambers 19b and 19c, respectively. The air pressure also serves to purge filter 7 of small particulates so that they are ready to repeat the next dosing sequence. After the purge step, the movable divider 32 is withdrawn from the forming cavity 19a by moving divider mounting plate 8 upward in direction C to its home position as shown in FIG. 8B. As shown in FIG. 8B, the movable dividers have created a interface line between powder blend volumes 1b and 2b during the filling operation.

The fact that two powdered formulations are deposited at one time is a major distinguishing feature of this invention over the existing sequential layer upon layer compression method, and it offers significant advantages. The fact that both components are dosed at one time greatly simplifies the manufacturing apparatus, and it can offer a higher tablet output from a given amount of equipment tooling.

In the above embodiment of the invention, a process of vacuum filling the nozzles is utilized. This filling method is advantageous in that it allows for very accurate filling of poorly flowing powder formulations. Poorly flowing and/or highly porous formulations are often required for manufacturing orally disintegrating tablets. These tablets often have a very soft, erodible construct to assist disintegration in the mouth. For tablet forms that do not require these attributes and/or that are constructed from more dense and compacted formulations, the vacuum filling method can optionally be replaced by merely tamping the powder blend beds. In such an embodiment, the vacuum source and filters are eliminated. The dose tubes are inserted into the powder blend bed, and the force of insertion and subsequent compaction make the powder blend stick to the inside of the nozzle cavity by the force of friction. In such an embodiment, ejector pins (not shown) may be substituted for the filters, residing in the same location with the dosing nozzles 3 and 4 to control volume of powder blend within each dosing nozzle. Such ejector pins may be attached to a plate that moves the ejector pins down at the appropriate time to evacuate the powder blend from the nozzle cavities.

Figure 9:
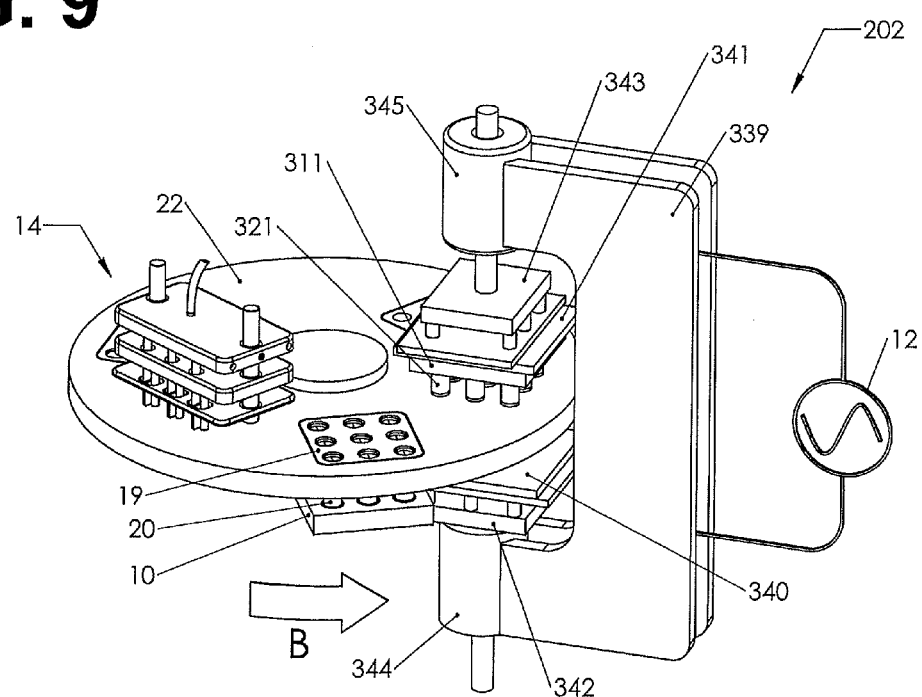
FIG. 9 is a perspective view of forming station 202.
Figure 11:
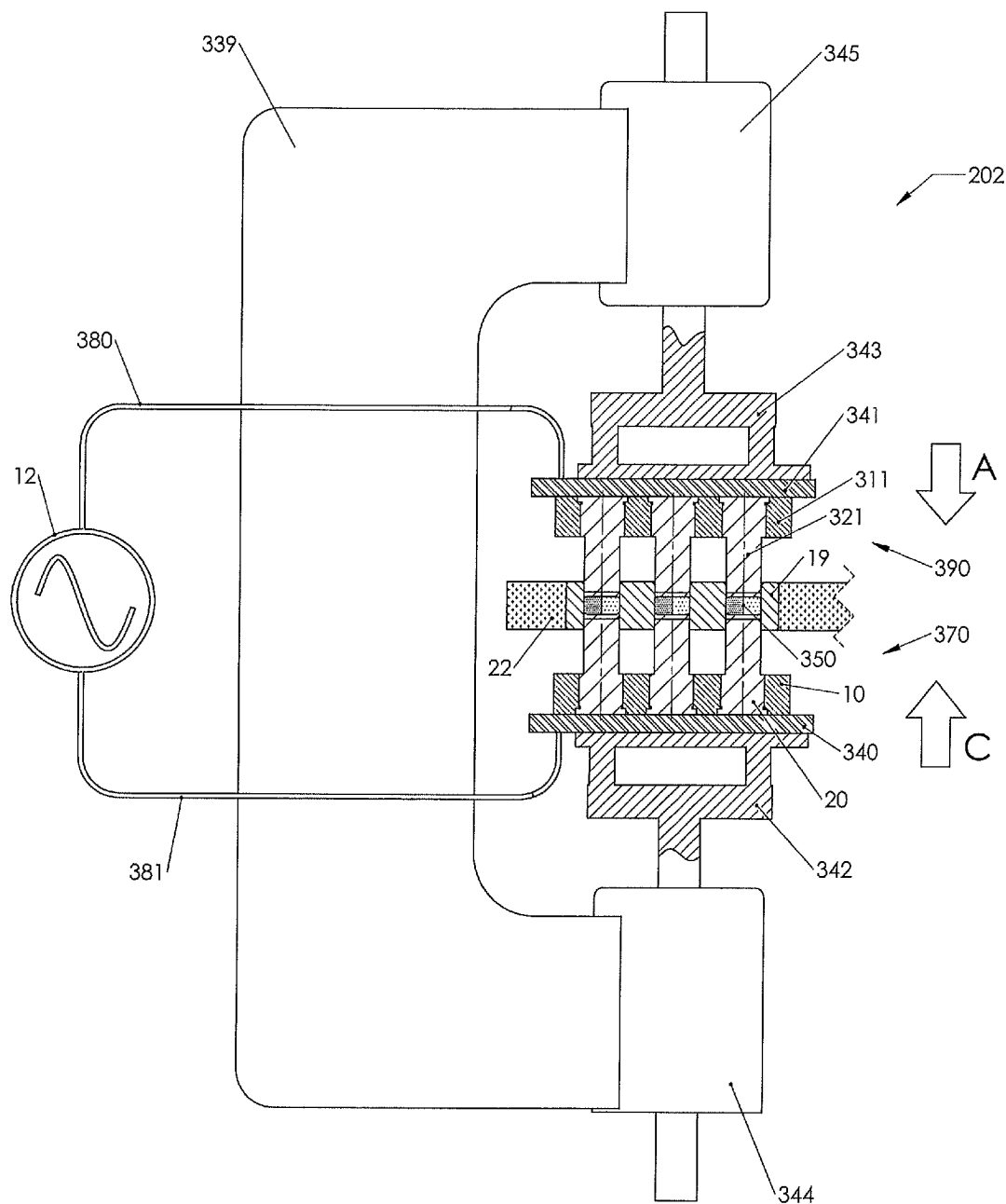
FIG. 11 is a cross section showing movable electrode plate 340 and movable electrode plate 341 in a closed position.

FIG. 9 depicts the die block 19 now filled with powder blend rotating in an indexing fashion over to the forming station 202 in direction B. FIG. 10 depicts a cross section through the forming station 202. Forming station 202 is comprised of a press frame 339, moving platen 343, moving platen 342, power cylinder 345, power cylinder 344, and upper forming tools 321 housed in upper tool holder 311. In one embodiment, the powder blend volumes 1b and 2b are shaped together by using power cylinders 345 and 344 to apply a force to forming tools 20 and 321. As the form tools move closer together (upper forming tools 321 moves in direction A and lower forming tools 20 moves in direction C), the powder blend volumes 1b and 2b are shaped in the form of the tablet 350 as shown in FIG. 11.

In one embodiment, radio frequency energy is used to add heat energy to the powder blends 1b and 2b to create a sintered tablet 350. In such an embodiment, RF generator 12 is depicted symbolically in FIG. 9 and FIG. 10. In one embodiment, the configuration of the RF generator 12 is a free running oscillator system. Such as system is typically composed of a power vacuum tube (such as a triode) and a DC voltage source (e.g., between 1000 and 8000 volts)

connected across the cathode and plate (anode). A tank circuit is often used to impose a sinusoidal signal upon the control grid and electrodes, thereby producing the necessary frequency (typically 13.56 MHZ or 27.12 MHZ) and high voltage field. An example of such RF generator is the COSMOS Model C10X16G4 (Cosmos Electronic Machine Corporation, Farmingdale, N.Y.). In another embodiment, RF energy can be provided by a 50 Ohm system composed of a waveform generator which feeds a radio frequency signal to power amplifiers which are coupled to the electrodes and the load by an impedance matching network.

In FIG. 10, movable electrode plate 340 and movable electrode plate 341 are shown mounted, respectively, to moving platens 342 and 343. The press is represented in its open position in FIG. 10. Linear movement of moving platens 343 and 342 and their respective attached movable electrode plates 341 and 340 is respectively generated by power cylinders 345 and 344, which can be a device such as air cylinders or servo motor. Moving platens 343 and 342 are electrically isolated from movable electrode plates 341 and 340, respectively. RF generator 12 is connected to the movable electrode plates 341 and 340 respectively through wires 380 and 381. A movable electrode assembly 390, movable in direction A, is shown in its up position, and movable electrode assembly 370, movable in direction C, is shown in its down position. Upper forming tools 321 and retainer plate 311 are attached to the movable electrode plate 341 and, consequently, move up and down with it. Powder blend volumes 1b and 2b are within die block 19.

FIG. 11 is a section view through the same RF station, but shows the movable electrode plates 341 and 340 in a closed position (having moved in directions A and C, respectively). pressing forming tools 321 and 20 towards each other to both shape and apply RF energy to powder blend volumes 1b and 2b. This RF energy heats powder blend volumes 1b and 2b to create a solid tablet 350. After the RF forming cycle is complete, the movable electrode assemblies 390 and 370 move back to their starting positions.

Figure 12A:
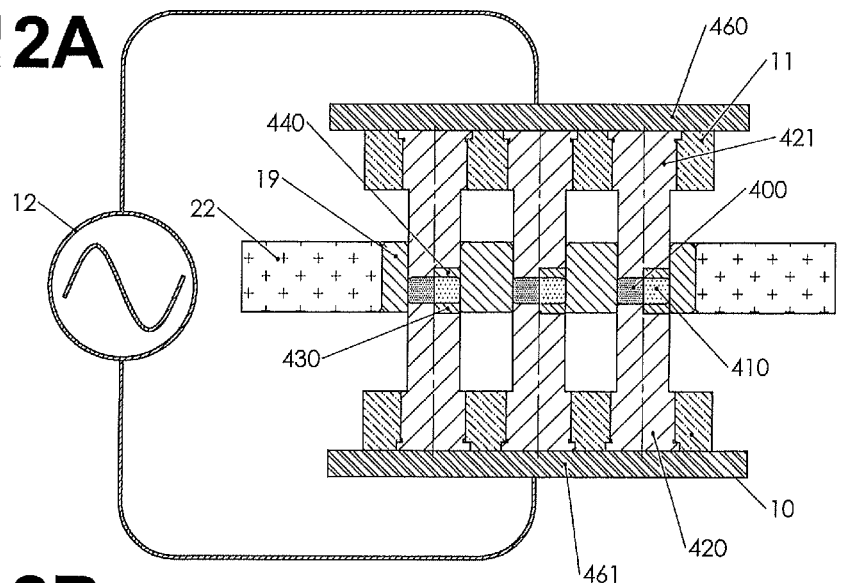
FIG. 12A is a cross section showing forming tools 420 and 421 with attachments 440 and 430 made of RF energy insulative material.

In an alternate embodiment illustrated in FIG. 12A, the forming tools can be constructed to achieve localized heating effects and can also be configured to shape the electric field that is developed across the tools. An RF generator 12 is connected to movable electrode plates 460 and 461. Forming tools 421 and 420 are constructed of an electrically conductive material, and they respectively have an attachment 440 and 430 which are made of electrical and RF energy insulative material (such as ceramic, Teflon®, polyethylene, or high density polyethylene). Die block 19 is also constructed of electrical and RF energy insulative material. This configuration creates regions on the forming tool where there is greater distance between the conductive portions of the forming tools 421 and 420 to weaken the electric field. This geometry will produce a tablet with lesser heating of the powder blend in area 410 since the electric field is weaker due to the greater distance between the conductive portions of forming tools 421 and 420. Area 400 of the powder blend receives the greater heating effect since the conductive portion of forming tools 421 and 420 are closer together, thereby making the electric field between them greater. This configuration allows a tablet to be formed with regions of different harnesses and/or textures.

Figure 12B:
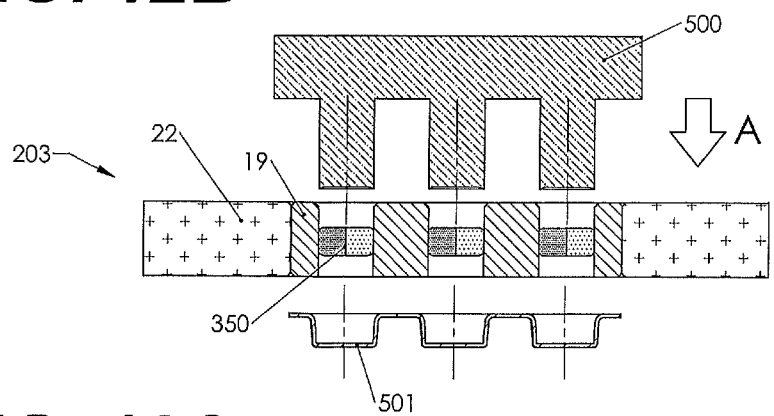
FIGS. 12B and 12C is a cross section of tablet ejection station 203.
Figure 12C:
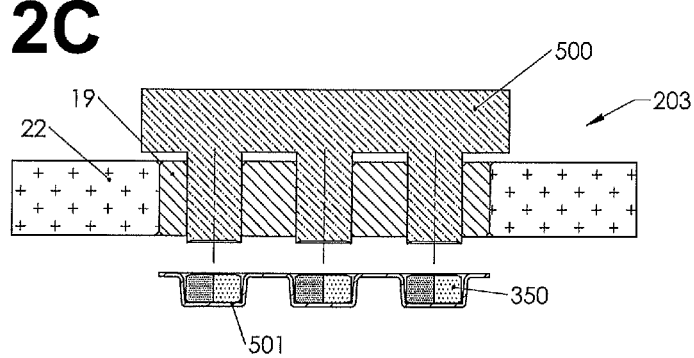

Once the tablets have been formed, the final step in the manufacturing process is to eject the tablets from the die block 19 using tablet ejection station 203. FIG. 12B shows the die block 19 with formed tablets 350 after they have indexed into the tablet ejection station 203. Ejector pins 500 move down in direction A to eject finished tablets 350 out of die block 19 into a package container 501 (e.g., a blister package) as shown in FIG. 12C. This direct placement of tablets into the package helps prevent breakage that could occur while using typical means such as feeders or by dumping tablets into transport drums.

Interface Between Regions of Tablet

Figure 13A:
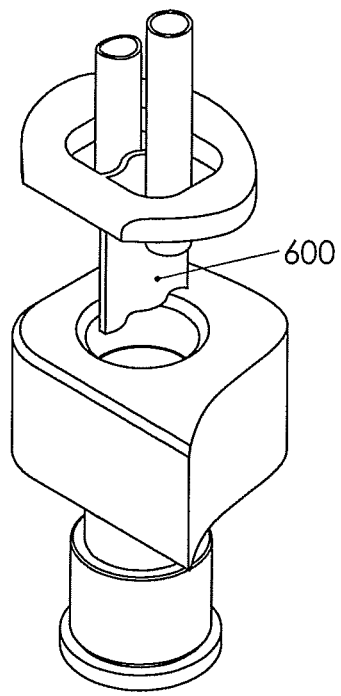
FIGS. 13A-C are a perspective view of various embodiment of divider plates.
Figure 13B:
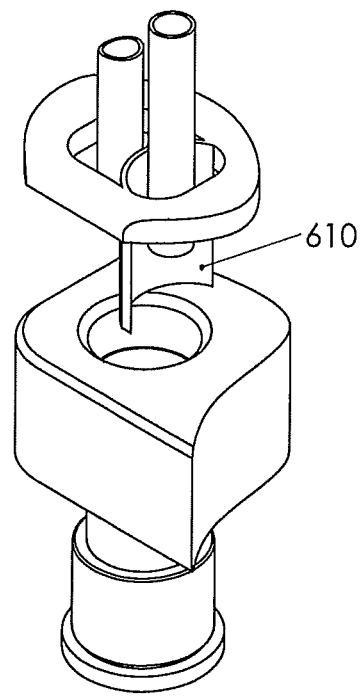

In FIG. 7B, the divider plate 32 in this embodiment has a straight, linear geometry and is positioned at the center of the cylindrical volume of the forming cavity 19a. In this configuration, a tablet, such as tablet 100 as shown in FIG. 1A, can be produced from the manufacturing operation, wherein the interface 103 between the first region 101 and second region 102 is along the diameter of the major face of the tablet. The divider plate, however, can have other geometries that are non-linear, such as angled, curved, or wave shaped. A tablet produced by wave shape divider plate is shown in FIG. 1B. The wave shape thus forms the curvilinear interface 114 between first region 112 and second region 113. FIG. 13A is an illustration of the wavy divider plate 600 that can be used to produce a tablet similar to the tablet of FIG. 1B. FIG. 13B depicts an arc-shaped divider plate 610 which can used to produce a tablet similar to the tablet of FIG. 1C having a curved interface 115.

Figure 13C:
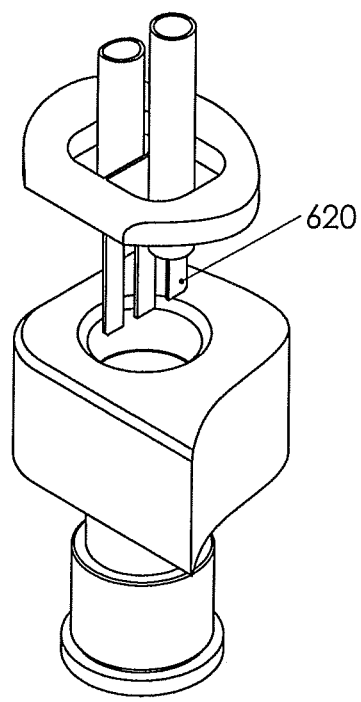

The divider plate functions to create a barrier between the powder blends during the filling operation. By preventing the intermingling of the two powder blends, a crisp interface is created. In one embodiment, a more blended interface may be desired, as depicted in FIG. 1D. To create the blended interface 119 depicted in the tablet on FIG. 1D, in one embodiment, a divider plate is not used. As such, when the dosing nozzles simultaneously deposit the powder blend together without a divider plate, the two powder blends intermingle within the die cavity. Since air pressure may be used in one embodiment of the dosing nozzle operation to blow the powder blend into the die cavity, the nozzle can also be configured to obtain swirling or turbulence effects to enhance intermingling of the regions. FIG. 13C depicts a further design variation where a divider plate 620 is used in the manufacturing sequence. It has been divided into segments where openings exist that create a tablet with staggered regions of crisp and blended interfaces. In this case, the resulting tablet would have crisp-blended-crisp-blended-crisp interface region between the two individual components.

Figure 14A:
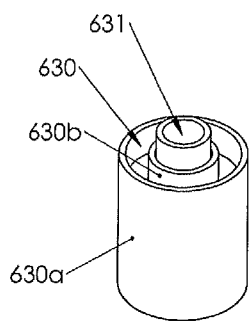
FIG. 14A is a perspective view of outer dosing nozzle 630 and inner dosing nozzle 631.
Figure 14B:
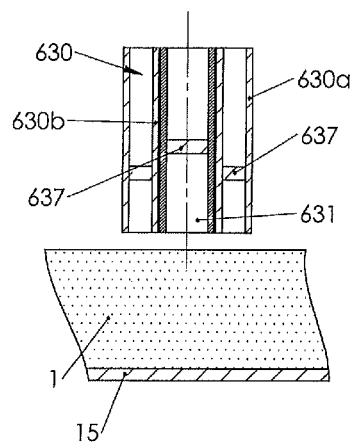
FIG. 14B-J are cross sections of outer dosing nozzle 630 and inner dosing nozzle 631.
Figure 14C:
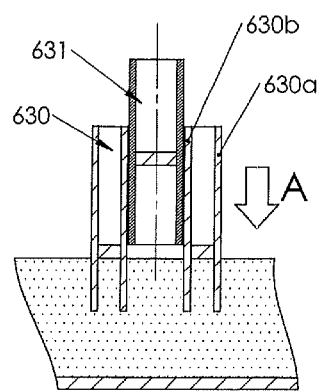
Figure 14D:
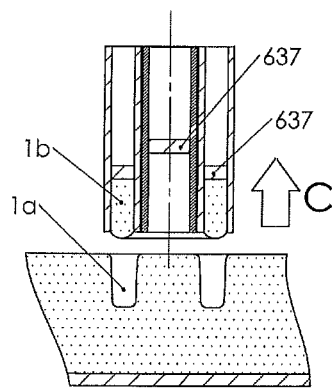
Figure 14E:
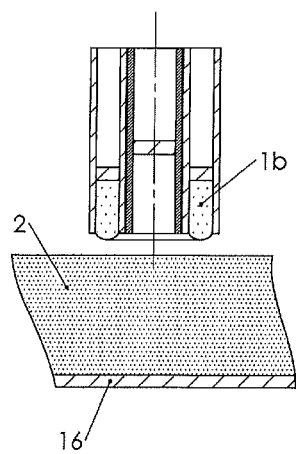
Figure 14F:
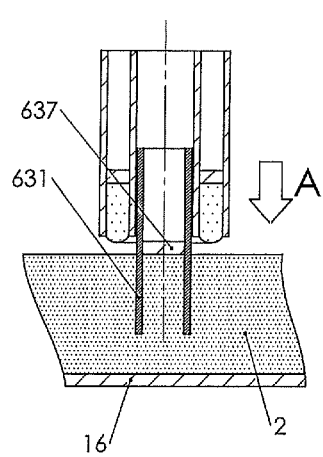
Figure 14G:
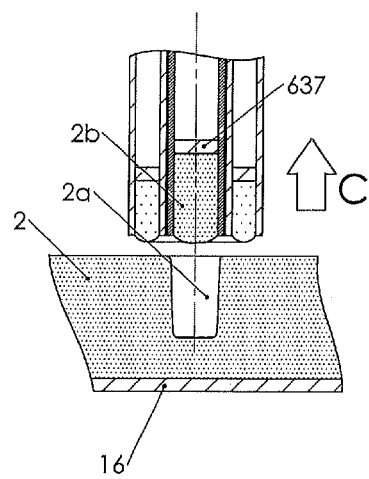
Figure 14H:
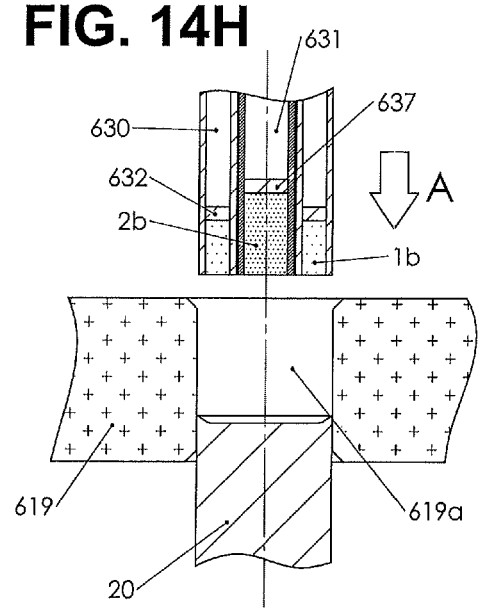
Figure 14I:
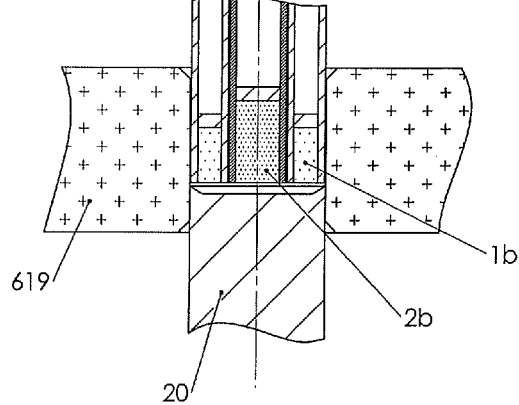
Figure 14J:
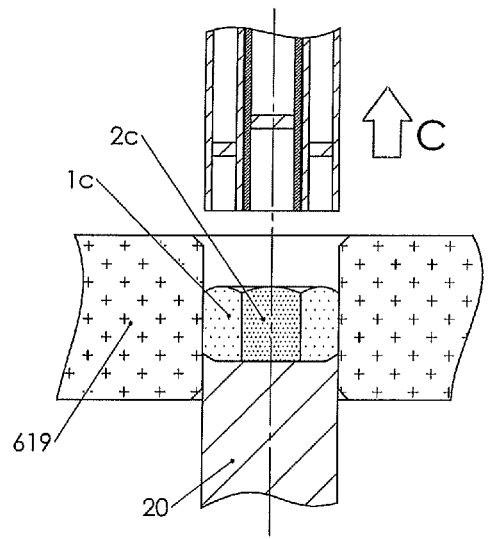

To produce the bull's eye tablet geometry that is illustrated in FIG. 1E, the dosing nozzle configuration as shown in FIG. 14A can be used. As shown in isometric view FIG. 14A, the dosing nozzles are comprised of concentric telescoping tubes. FIG. 14B is a section through the concentric dosing nozzles. In this embodiment, an outer dosing nozzle 630 is comprised of an outer tube 630a and an inner tube 630b and is movable and independent of inner dosing nozzle 631 which is also independently movable. In this embodiment, as shown in FIG. 14B-14D, the outer dosing nozzle 630 is movable in directions A and C to obtain powder blend volume 1b from powder blend bed 1 within first powder blend tray 15, leaving vacant space 1a. As shown in FIGS. 14E-14G, inner dosing nozzle 631 is also movable in directions A and C to obtain powder blend 2b from powder blend bed 2 within first powder blend tray 16, leaving vacant space 2a. The amount of powder blend volumes 1b and 2b is dependent upon the placement of filters 637. As shown in FIGS. 14H-14J, both inner nozzle 631 and outer nozzle 630 are movable in directions A and C in order to deposit powder blend volumes 1b and 2b simultaneously into a die cavity 19a within die block 19 to achieve the desired bull's eye powder blend distribution.

In one embodiment, a lubricant is added to forming cavity prior to the addition of the flowable powder blend. This lubricant may be a liquid or solid. Suitable lubricants include, but are not limited to; solid lubricants such as magnesium stearate, starch, calcium stearate, aluminum stearate and stearic acid; or liquid lubricants such as but not limited to simethicone, lecithin, vegetable oil, olive oil, or mineral oil. In certain embodiments, the lubricant is added at a percentage by weight of the tablet of less than 5 percent, e.g. less than 2 percent, e.g. less than 0.5 percent. In certain embodiments, the presence of a hydrophobic lubricant can disadvantageously compromise the disintegration or dissolution properties of a tablet. In one embodiment the tablet is substantially free of a hydrophobic lubricant. Examples of hydrophobic lubricants include magnesium stearate, calcium stearate and aluminum stearate.

Manufacturing Method for Single Region Tablets

Figure 15A:
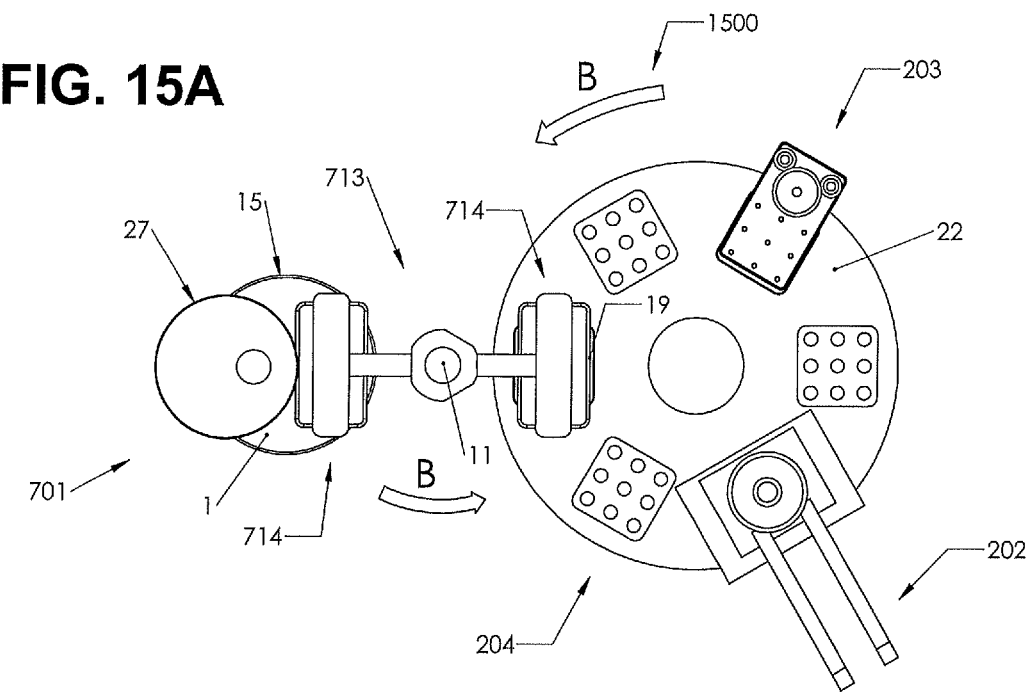
FIG. 15A is an overhead view of multi-component tablet machine 1500.
Figure 15B:
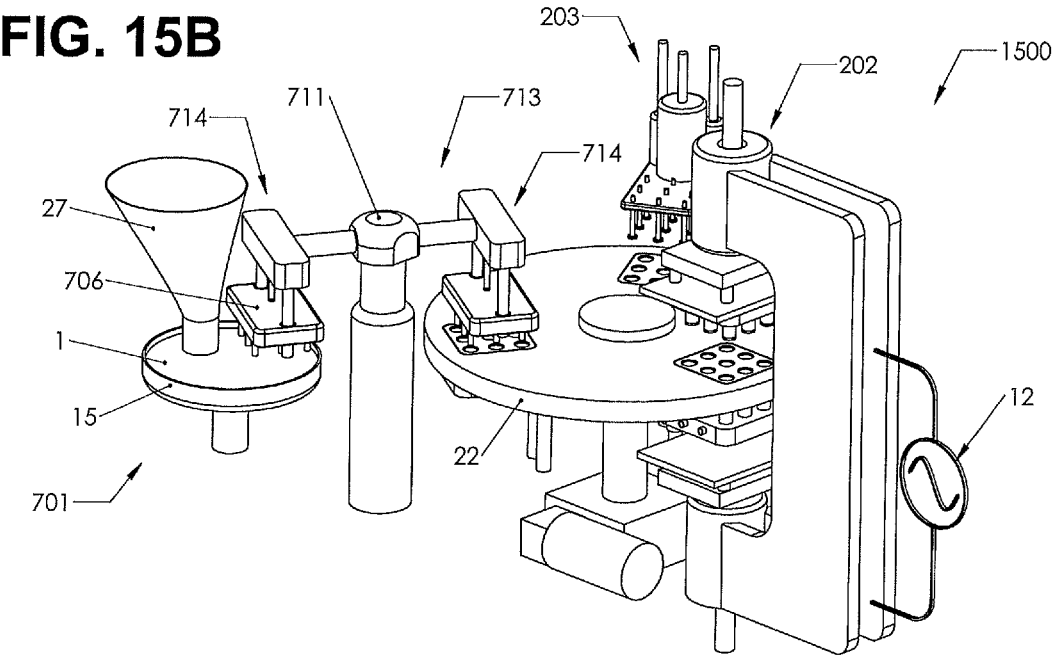
FIG. 15B is a perspective view of multi-component tablet machine 1500.

In one aspect, the present invention features a machine capable of producing single region tablet. One embodiment of such a single-region tablet machine 1500 is depicted in FIGS. 15A and 15B, which is similar to the multi-region tablet machine 200 depicted above in FIGS. 2A and 2B. FIG. 15A illustrates a plan view of this embodiment, and FIG. 15B illustrates a three dimensional view of this embodiment. The machine of FIG. 15A and FIG. 15B differs from that of FIG. 2A and FIG. 2B in that the powder blend dosing station 701 is designed to accurately dose only a single powder blend. In a preferred embodiment, the dosing head assembly 701 is comprised of two identical dosing modules 714 arrayed radially from a central hub 711. In this embodiment, the rotary dose head assembly sequentially indexes first over powder blend bed 1 to obtain a volume of powder blend from powder blend bed 1.

Figure 16A:
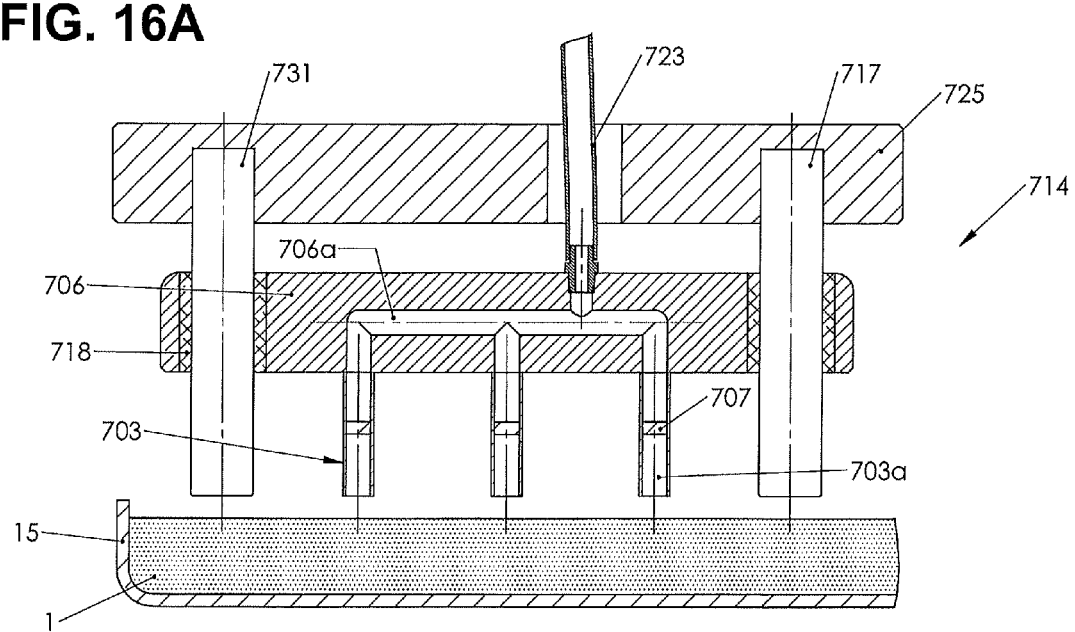
FIGS. 16A-16B are cross sections of dosing module 714 over first powder tray 15.

FIG. 16A shows a cross section through one of the dosing modules 714. In this view, the dosing module 714 is positioned over the first powder blend tray 15, ready to begin a first step in the dosing sequence. The dosing module 714 is comprised of a plurality of dosing nozzles 703, which have a hollow tube shape. Within each nozzle is a filter 707 which have their position within the tube being adjustable so as to set the desired dose volume of nozzle cavities 703a. Each nozzle is connected to flow passageways 706a, which allow vacuum to be drawn via vacuum tube 723. The dosing nozzles 703 are mounted to manifold plate 706, which is moveable linearly and are guided with bearings 718 upon shaft 717 and shaft 731.

Figure 16B:
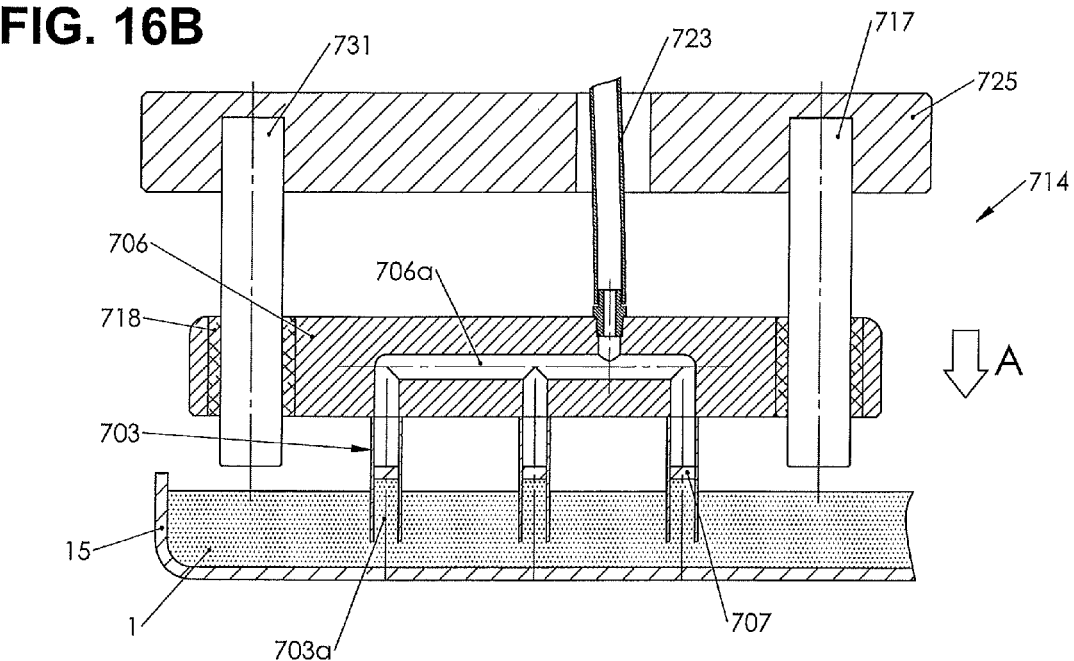
Figure 17A:
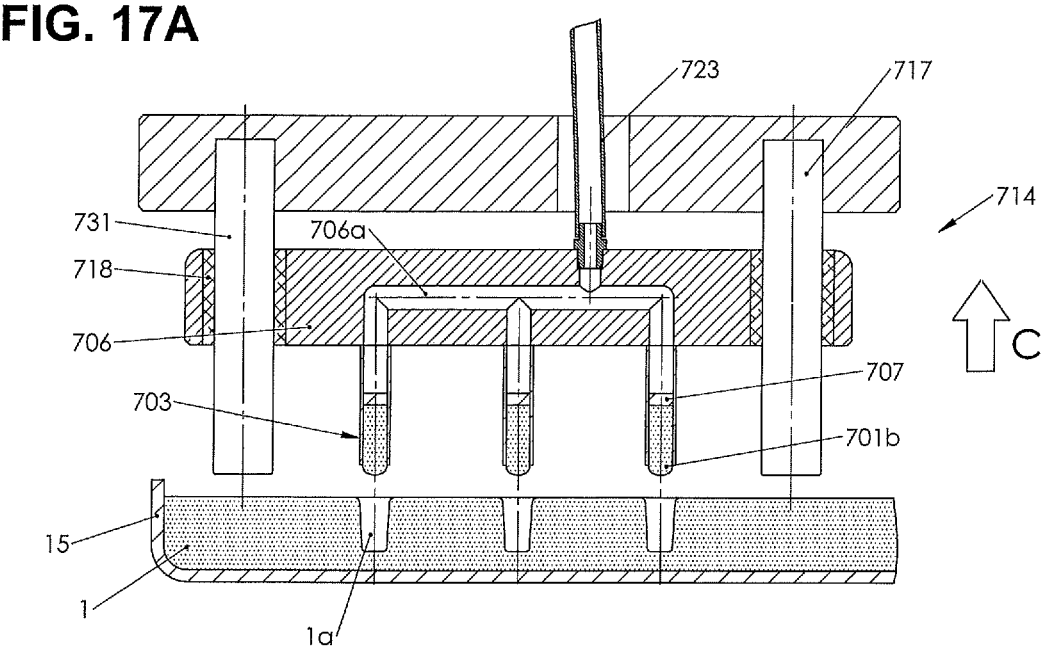
FIG. 17A is a cross section of dosing module 714 over first powder tray 15.

FIG. 16B shows manifold plate 706 and attached dosing nozzles 703 after they have moved down in direction A and penetrated into powder blend bed 1. At this point the vacuum source which is controlled via an external valve (not shown), is switched on, pulling a vacuum through vacuum tube 723. Powder blend from the powder blend bed 1 is sucked into the nozzle cavity 703a. Filter 707 prevents such powder blend from passing beyond nozzle cavity 703a. The volume of powder blend within nozzle cavity 703a can be modified by repositioning filter 707 within dosing nozzle 703. Once dosing is complete, the manifold plate 706 is retracted in direction C to the starting position as shown in FIG. 17A. The vacant space 1a left in the powder blend bed 1 as a result of the filling operation is also shown. As shown in FIG. 17A, nozzle cavity 703a is now filled with powder blend volume 701b.

Figure 17B:
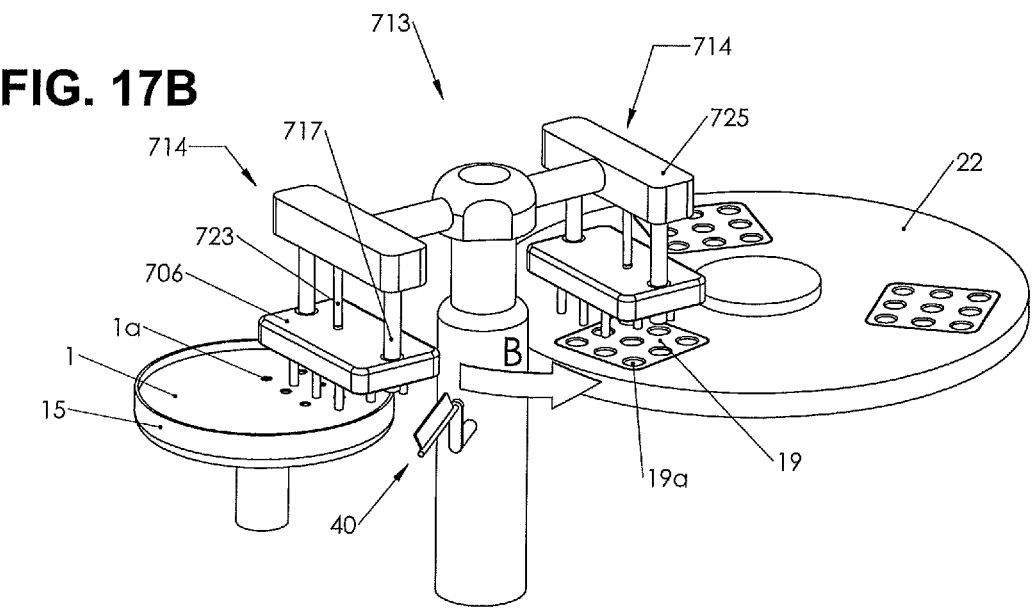
FIG. 17B is a perspective view of dosing module 714 moving from the first powder tray 15 to a position over the die block 19.
Figure 18A:
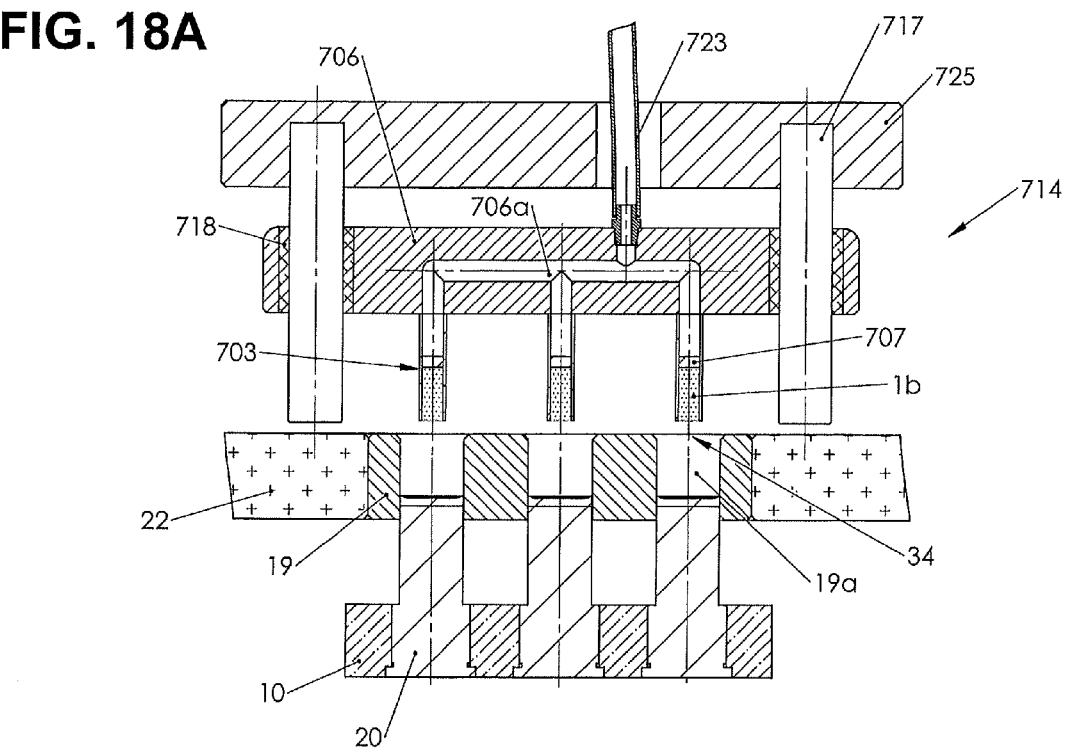
FIGS. 18A and 18B are cross sections of dosing module 714 over die block 19.

FIG. 17B is a schematic representation of one of the dosing modules 714 moving from the first powder tray 15 to a position over the die block 19. Die block 19 is mounted with dial plate 22 which is part of the rotary table assembly 204. The dial plate 22 is synchronized with the dosing head assembly 701 (as shown in FIG. 15B) such that after an indexing motion, dosing module 714 is positioned over the forming cavity 19a, as shown in cross section in FIG. 18A. As shown in this illustration, nozzle cavities 703a (shown empty in FIG. 16A) are now filled with powder volume 701b. Lower forming tools 20 are then inserted through the bottom of die block 19. Forming tools 20 are housed in tool holder block 10.

Figure 18B:
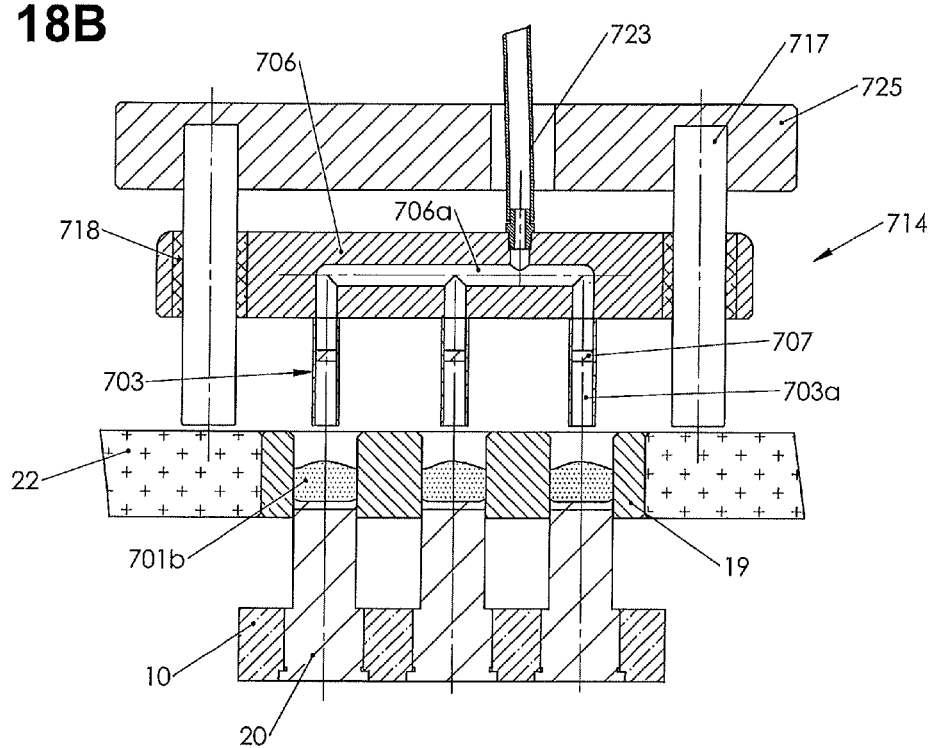

FIG. 18B illustrates the filling sequence of the operation. Here dosing nozzles 3 are shown evacuated with the powder blend volume 701b now residing within die block 19. To achieve the full and complete discharge of the powder blend from the nozzles, an external valve switches from a vacuum source to a pressure source, sending air pressure through vacuum tube 723. This air pressure passes through filters 707 and blows the powder blend volume 701b into the die block 19.

Figure 19:
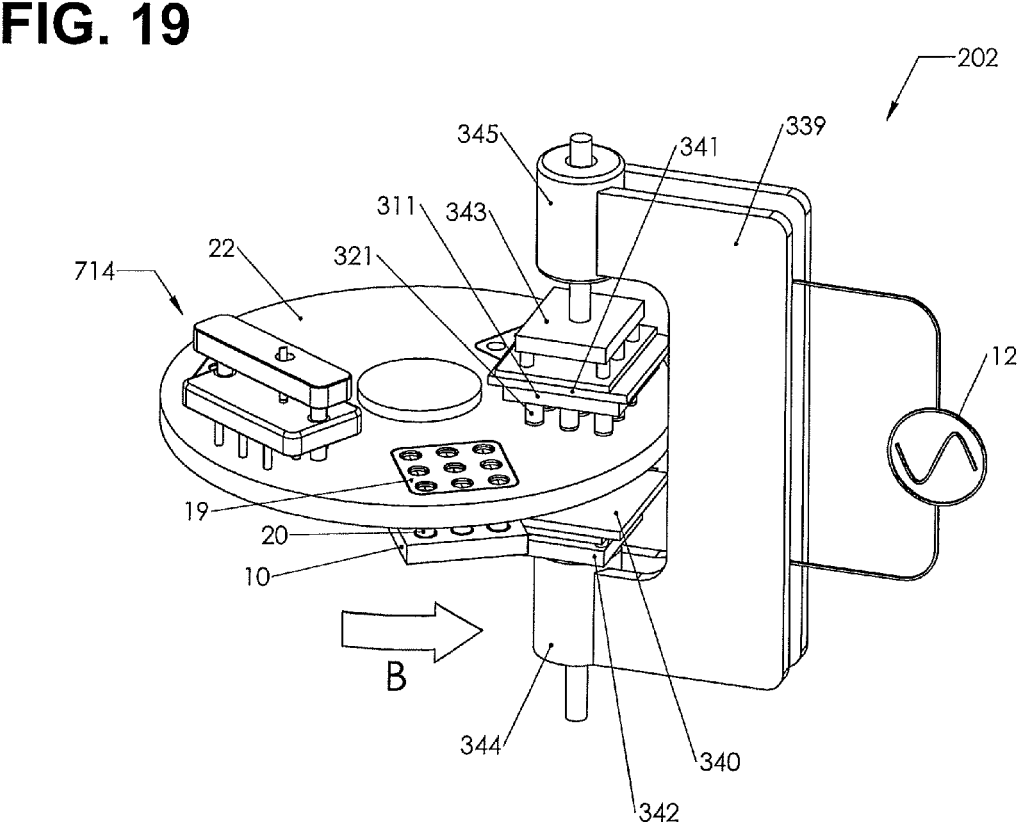
FIG. 19 is a perspective view of forming station 202.
Figure 20:
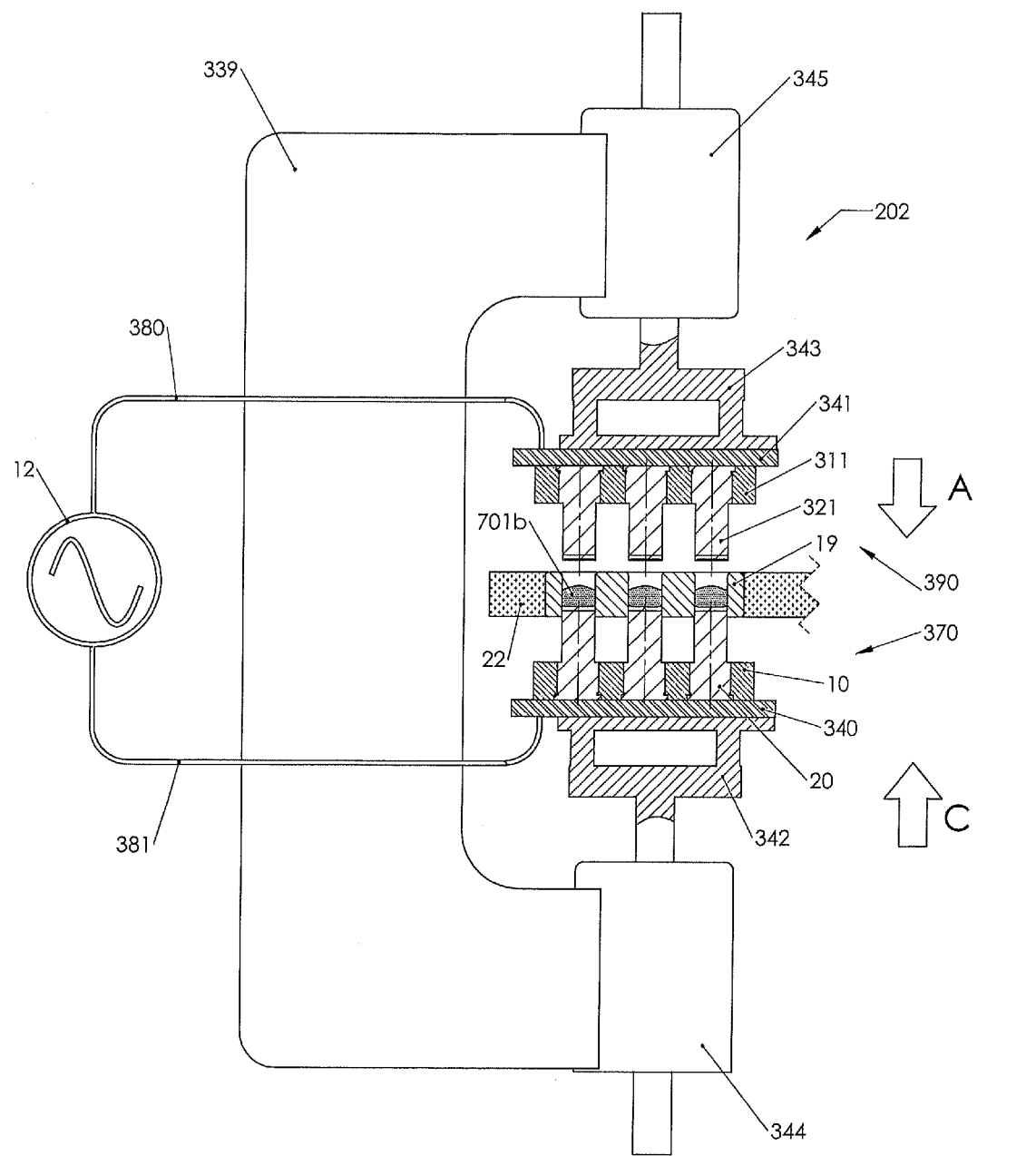
FIG. 20 is a cross section showing movable electrode plate 340 and movable electrode plate 341 in an open position.
Figure 21:
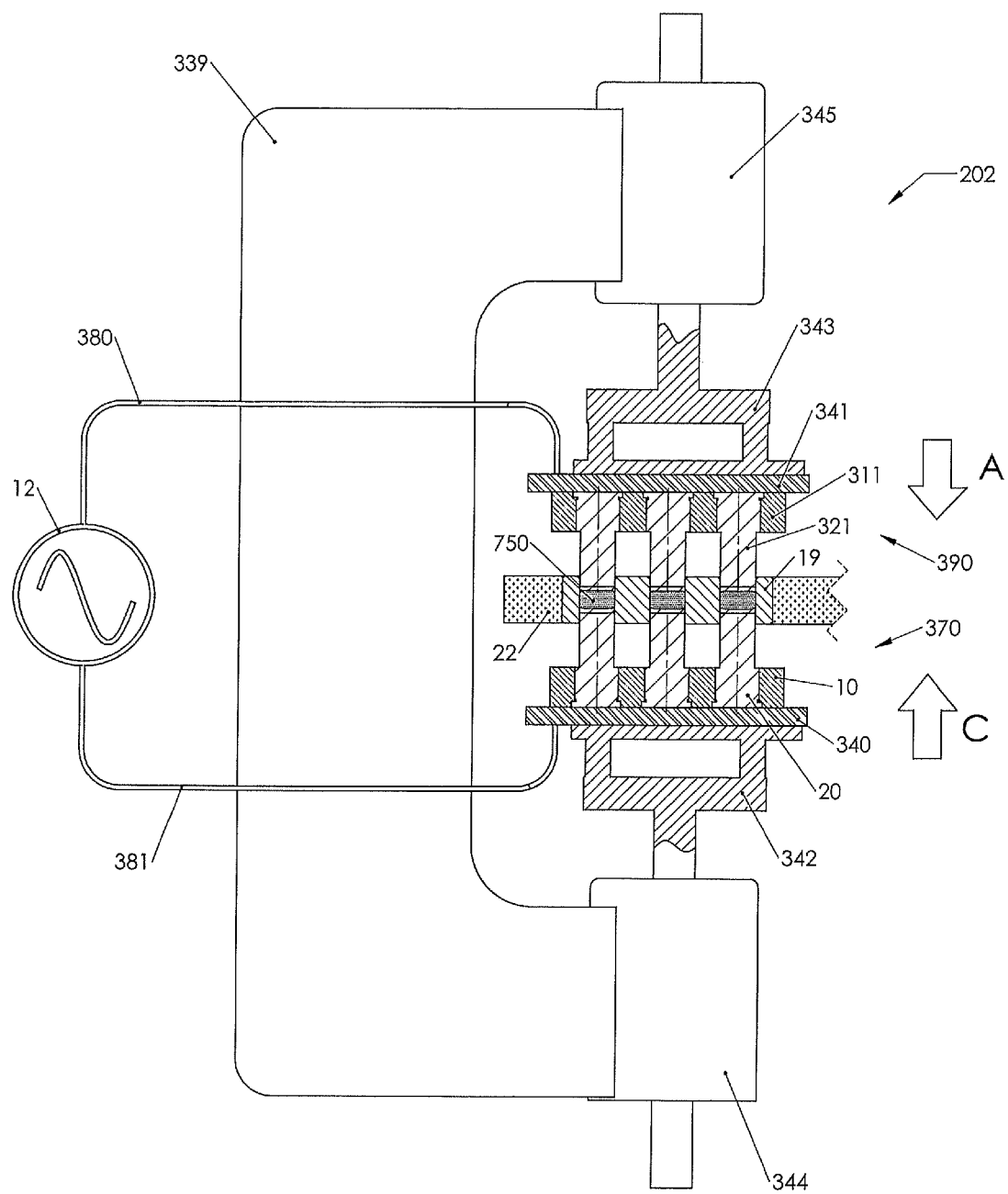
FIG. 21 is a cross section showing movable electrode plate 340 and movable electrode plate 341 in a closed position.

FIGS. 19-20 depicts the die block 19, now filled with powder blend, rotating in an indexing fashion over to the forming station 202 (discussed above). As the forming tools move closer together along directions A and C, the powder blend volumes 1b are shaped to the form of the tablet 750 (as shown in FIG. 21).

Figure 22A:
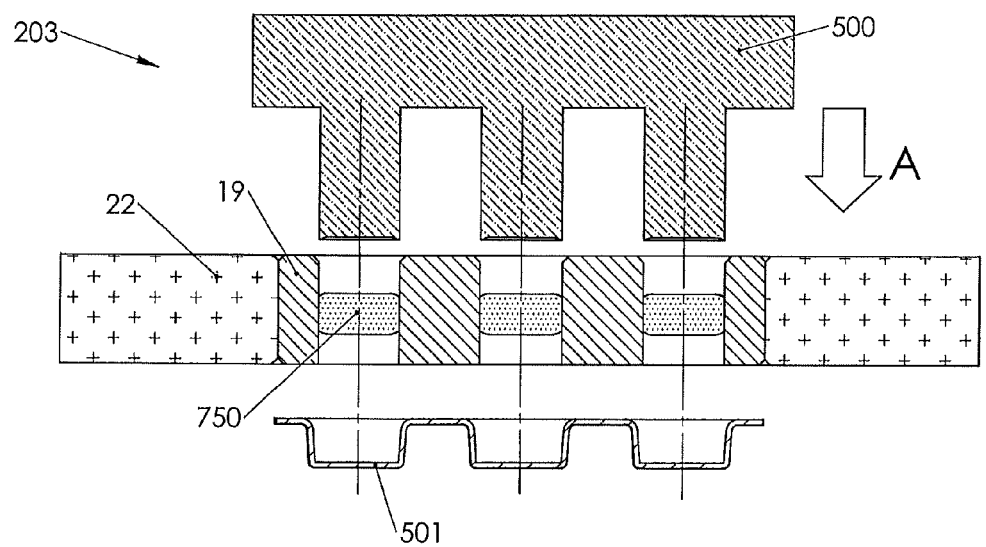
FIGS. 22A and 22B are a cross section of tablet ejection station 203.
Figure 22B:
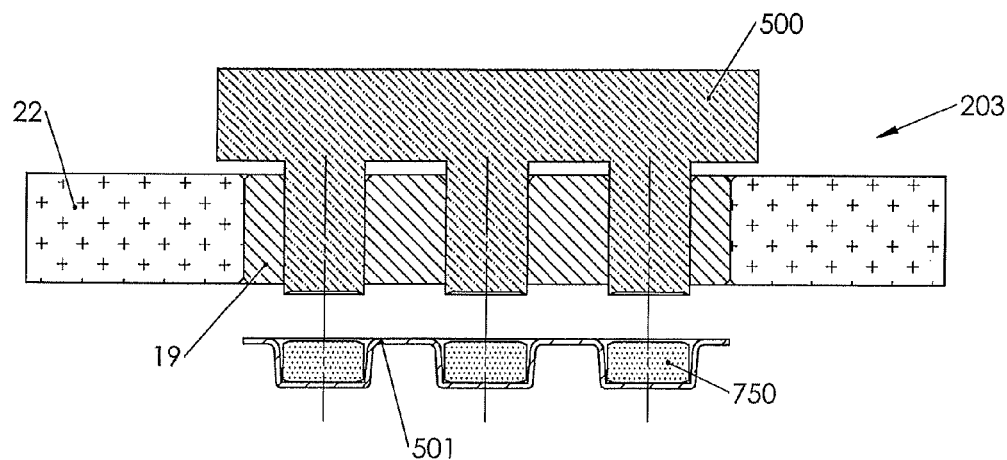

Once the tablets have been formed, the final step in the manufacturing process is to eject the tablets from the die block 19 using tablet ejection station 203 (discussed above). FIG. 22A shows the die block 19 with formed tablets 750 after they have indexed into the tablet ejection station 203. Ejector pins 500 move down in direction A to eject finished tablets 750 out of die block 19 into a package container 501 (e.g., a blister package) as shown in FIG. 22. This direct placement of tablets into the package helps prevent breakage that could occur while using typical means such as feeders or by dumping tablets into transport drums.

Radiofrequency Heating of Tablet Shape to Form Tablet

In one embodiment, Radiofrequency heating is utilized in the manufacture of the tablets. Radiofrequency heating generally refers to heating with electromagnetic field at frequencies from about 1 MHz to about 100 MHz. In one embodiment of the present invention, the RF-energy is within the range of frequencies from about 1 MHz to about 100 MHz (e.g., from about 5 MHz to 50 MHz, such as from about 10 MHz to about 30 MHz). The RF-energy is used to impart energy (e.g., to heat) the powder blend(s). The degree of any compaction to the powder blend, the type and amount of materials within the powder blend, and the amount of RF energy used can determine the hardness and/or type of tablet, such as whether an oral disintegrating tablet, a soft chewable tablet is manufactured, a gum, or a lozenge is manufactured.

RF energy generators are well known in the art. Examples of suitable RF generators include, but are not limited to, COSMOS Model C10X16G4 (Cosmos Electronic Machine Corporation, Farmingdale, N.Y.).

In one embodiment, the upper and lower forming tools serve as the electrodes (e.g., they are operably associated with the RF energy source) through which the RF energy is delivered to the tablet shape. In one embodiment, there is direct contact between at least one RF electrode (e.g., forming tool) and the tablet shape. In another embodiment, there is no contact between any of the RF electrode (e.g., forming tools) and the tablet shape. In one embodiment, the RF electrodes are in direct contact with the surface of the tablet shape when the RF energy is added. In another embodiment, the RF electrodes are not in contact (e.g., from about 1 mm to about 1 cm from the surface of the tablet shape) during the addition of the RF energy.

In one embodiment, the RF energy is delivered while the tablet shape is being formed. In one embodiment, the RF energy is delivered once the tablet shape is formed. In one embodiment, the RF energy is delivered after the tablet shape has been removed from the die.

In one embodiment, the RF energy is applied for a sufficient time to bind substantially all (e.g., at least 90%, such as at least 95%, such as all) of the powder blend the tablet shape. In one embodiment, the RF energy is applied for a sufficient time to bind only a portion (e.g., less than 75%, such as less than 50%, such as less than 25%) of the powder blend within the tablet shape, for example only on a portion of the tablet shape, such as the outside of the tablet shape.

In alternate embodiment of the invention, the forming tools can be constructed to achieve localized heating effects and can also be configured to shape the electric field that is developed across the forming tools. Examples of such forming tools are depicted in FIGS. 11-14 of US Patent Application No. 2011/0068511.

In one embodiment, to help reduce sticking, the tablet is cooled within the forming cavity to cool and/or solidify the tablet. The cooling can be passive cooling (e.g., at room temperature) or active cooling (e.g., coolant recirculation cooling). When coolant recirculation cooling is used, the coolant can optionally circulate through channels inside the forming tools (e.g., punches or punch platen) and/or die or die block. In one embodiment, the process uses a die block having multiple die cavities and upper and lower punch platens having multiple upper and lower punched for simultaneous forming of a plurality of tablets wherein the platens are actively cooled.

In one embodiment, there is a single powder blend forming the tablet shape which is then heated with the RF energy. In another embodiment, the tablet is formed of at least two different powder blends, at least one powder blend being RF-curable and at least one formulation being not RF-curable. When cured with RF energy, such tablet shape develops two or more dissimilarly cured zones. In one embodiment, the outside area of the tablet shape is cured, while the middle of the tablet shape is not cured. By adjusting the focus of the RF heating and shape of the RF electrodes, the heat delivered to the tablet shape can be focused to create customized softer or harder areas on the finished tablet.

In one embodiment the RF energy is combined with a second source of heat including but not limited to infrared, induction, or convection heating. In one embodiment, the addition of the second source of heat is particularly useful with a secondary non-RF-meltable binder present in the powder blend.

Microwave Heating of Tablet Shape to Form Tablet

In one embodiment, microwave energy is used in place of radiofrequency energy to manufacture the dosage form (e.g., tablet). Microwave heating generally refers to heating with electromagnetic field at frequencies from about 100 MHz to about 300 GHz. In one embodiment of the present invention, the microwave energy is within the range of frequencies from about 500 MHz to about 100 GHz (e.g., from about 1 GHz to 50 GHz, such as from about 1 GHz to about 10 GHz). The microwave energy is used to heat the powder blend. In such an embodiment, a microwave energy source and microwave electrodes are used in the machine used to manufacture the dosage form.

Inserts within Tablet Shape

In one embodiment, an insert is incorporated into the tablet shape before the RF energy is delivered. Examples include solid compressed forms or beads filled with a liquid composition. Such incorporation of an insert is depicted in FIGS. 3A-3G.

In one embodiment the pharmaceutically active agent is in the form of a gel bead, which is liquid filled or semi-solid filled. The gel bead(s) are added as a portion of the powder blend. In one embodiment, the tablet of this invention has the added advantage of not using a strong compaction step, allowing for the use of liquid or semisolid filled particles or beads which are deformable since they will not rupture following the reduced pressure compaction step. These bead walls may contain gelling substances such as: gelatin; gellan gum; xanthan gum; agar; locust bean gum; carrageenan; polymers or polysaccharides such as but not limited to sodium alginate, calcium alginate, hypromellose, hydroxypropyl cellulose and pullulan; polyethylene oxide; and starches. The bead walls may further contain a plasticizer such as glycerin, polyethylene glycol, propylene glycol, triacetin, triethyl citrate and tributyl citrate. The pharmaceutically active agent may be dissolved, suspended or dispersed in a filler material such as but not limited to high fructose corn syrup, sugars, glycerin, polyethylene glycol, propylene glycol, or oils such as but not limited to vegetable oil, olive oil, or mineral oil.

In one embodiment, the insert is substantially free of RF-absorbing ingredients, in which case application of the RF energy results in no significant heating of the insert itself. In other embodiments, the insert contains ingredients and are heated upon exposure to RF energy and, thus, such inserts can be used to heat the powder blend.

Effervescent Couple

In one embodiment, the powder blend further contains one or more effervescent couples. In one embodiment, effervescent couple contains one member from the group consisting of sodium bicarbonate, potassium bicarbonate, calcium carbonate, magnesium carbonate, and sodium carbonate, and one member selected from the group consisting of citric acid, malic acid, fumaric acid, tartaric acid, phosphoric acid, and alginic acid.

In one embodiment, the combined amount of the effervescent couple(s) in the powder blend/tablet is from about 2 to about 20 percent by weight, such as from about 2 to about 10 percent by weight of the total weight of the powder blend/tablet.

Orally Disintegrating Tablet

In one embodiment, the tablet is designed to disintegrate in the mouth when placed on the tongue in less than about 60 seconds, e.g. less than about 45 seconds, e.g. less than about 30 seconds, e.g. less than about 15 seconds.

In one embodiment, the tablet meets the criteria for Orally Disintegrating Tablets (ODTs) as defined by the draft Food and Drug Administration guidance, as published in April, 2007. In one embodiment, the tablet meets a two-fold definition for orally disintegrating tablets including the following criteria: 1) that the solid tablet is one which contains medicinal substances and which disintegrates rapidly, usually within a matter of seconds, when placed upon the tongue and 2) be considered a solid oral preparation that disintegrates rapidly in the oral cavity, with an in vitro disintegration time of approximately 30 seconds or less, when based on the United States Pharmacopeia (USP) disintegration test method for the specific medicinal substance or substances.

Tablets Coatings

In one embodiment, the tablet includes an additional outer coating (e.g., a translucent coating such as a clear coating) to help limit the friability of the tablet. Suitable materials for translucent coatings include, but are not limited to, hypromellose, hydroxypropylcellulose, starch, polyvinyl alcohol, polyethylene glycol, polyvinylalcohol and polyethylene glycol mixtures and copolymers, and mixtures thereof. Tablets of the present invention may include a coating from about 0.05 to about 10 percent, or about 0.1 to about 3 percent by weight of the total tablet.

Hardness/Density of Tablet

In one embodiment, the tablet is prepared such that the tablet is relatively soft (e.g., capable of disintegrating in the mouth or being chewed). In one embodiment, the hardness of the tablet of the present invention uses a Texture Analyzer TA-XT2i to measure the peak penetration resistance of the tablet. The texture analyzer is fitted with a flat faced cylindrical probe having a length equal to or longer than the thickness of the tablet (e.g., 7 mm) and a diameter of 0.5 mm. Tablet hardness is determined by the maximum penetration force of a probe boring through the center of a major face of the tablet or the center of the region on the major face when the major face has more than one region, where the probe is a 0.5-mm diameter, stainless steel, cylindrical wire with a blunt end and the tablet is supported by a solid surface having a 2-mm diameter through-hole centered in a counter bore having a diameter slightly greater than that of the tablet, for example 0.51 inches for a 0.5 inch diameter tablet. The probe, tablet, counter-bore, and 2-mm through hole are all concentric to one another. The texture analyzer is employed to measure and report the force in grams as the probe moves at 0.1 millimeters per second through the tablet, until the probe passes through at least 80% of the thickness of the tablet. The maximum force required to penetrate the tablet is referred to herein as the peak resistance to penetration ("peak penetration resistance").

In one embodiment, the peak penetration resistance at the center of a major face is from about 2 grams to about 500 grams, such as from about 50 grams to about 600 grams, such as from about 100 grams to about 300 grams. In one embodiment, one region of the tablet has a peak penetration resistance that is greater than the peak penetration resistance of the other region of the tablet (e.g., at least 10% greater, such as at least 25% greater, such as at least 50% greater, such as at least 100% greater).

In one embodiment, the density of the tablet is less than about 0.8 g/cc, such as less than about 0.7 g/cc. In one embodiment, one region of the tablet has a density that is greater than the density of the other region of the tablet (e.g., at least 5% greater, such as at least 10% greater, such as at least 25% greater, such as at least 50% greater).

In one embodiment, the tablets have a friability of less than 10 percent, such as less than 5 percent, such as less than 1 percent. As used herein, "friability" is measured using the USP 24 NF 29 Tablet Friability (Section 1216) with the modification of using 3 tablets for 10 rotations (unless otherwise noted) rather than 10 tablets for 100 rotations.

Use of Tablet

The tablets may be used as swallowable, chewable, or orally disintegrating tablets to administer the pharmaceutically active agent.

In one embodiment, the present invention features a method of treating an ailment, the method including orally administering the above-described tablet wherein the tablet includes an amount of the pharmaceutically active agent effective to treat the ailment. Examples of such ailments include, but are not limited to, pain (such as headaches, migraines, sore throat, cramps, back aches and muscle aches), fever, inflammation, upper respiratory disorders (such as cough and congestion), infections (such as bacterial and viral infections), depression, diabetes, obesity, cardiovascular disorders (such as high cholesterol, triglycerides, and blood pressure), gastrointestinal disorders (such as nausea, diarrhea, irritable bowel syndrome and gas), sleep disorders, osteoporosis, and nicotine dependence.

In one embodiment, the method is for the treatment of an upper respiratory disorder, wherein the pharmaceutically active agent is selected from the group of phenylephrine, cetirizine, loratadine, fexofenadine, diphenhydramine, dextromethorphan, chlorpheniramine, chlophedianol, and pseudoephedrine.

In this embodiment, the "unit dose" is typically accompanied by dosing directions, which instruct the patient to take an amount of the pharmaceutically active agent that may be a multiple of the unit dose depending on, e.g., the age or weight of the patient. Typically the unit dose volume will contain an amount of pharmaceutically active agent that is therapeutically effective for the smallest patient. For example, suitable unit dose volumes may include one tablet.

EXAMPLES

Specific embodiments of the present invention are illustrated by way of the following examples. This invention is not confined to the specific limitations set forth in these examples.

Example 1

Manufacture of Red Powder Blend Containing Loratadine

The loratadine powder blend for an orally disintegrating tablet, containing the ingredients of Table 1, is manufactured as follows:

TABLE 1

Loratadine Powder Blend Formulation

| Ingredient | G/Batch | mg/Tablet | % per tablet |
|---|---|---|---|
| Erythritol[1] | 61.47 | 129.50 | 61.47 |
| Loratadine | 4.75 | 10.0 | 4.75 |
| Maltodextrin[2] | 33.23 | 70.00 | 33.23 |
| Red Colorant | 0.04 | 0.075 | 0.04 |
| Sucralose USP | 0.14 | 0.3 | 0.14 |
| Mint Flavor[3] | 0.38 | 0.8 | 0.38 |
| Total | 100.0 | 210.68 | 100.0 |

[1]Commercially available from Corn Products in Westchester, IL as Erysta 3656 DC (80% erythritol)
[2]Commercially available from National Starch in Bridgewater, NJ
[3]Commercially available from International Flavors and Fragrances in New York, NY First, the sucralose, colorant, and flavor were placed together into a 500 cc sealable plastic bottle. The mixture was then blended end-over-end manually for approximately 2 minutes. The resulting mixture, the erythritol, loratadine, and the maltodextrin were then added to another 500 cc sealable plastic bottle and mixed end-over-end manually for approximately 5 minutes.

Example 2

Manufacture of White Powder Blend Containing Acetaminophen

The acetaminophen powder blend for a bisected orally disintegrating tablet, containing the ingredients of Table 2, was manufactured as follows. The sucralose, and flavor from the formula in Table 2 were passed through a 20 mesh screen. The sieved materials were placed into a 500 cc plastic bottle and blended end over end with the maltodextrin, erythritol and encapsulated acetaminophen in Table 2.

TABLE 2

Acetaminophen Powder Blend Formulation

| Ingredient | G/Batch | mg/Tablet | % per tablet |
|---|---|---|---|
| Erythritol[1] | 44.72 | 129.50 | 44.72 |
| Encapsulated Acetaminophen | 30.73 | 89.01 | 30.73 |
| Maltodextrin[2] | 24.17 | 70.00 | 24.17 |
| Sucralose USP | 0.10 | 0.3 | 0.10 |
| Mint Flavor[3] | 0.28 | 0.8 | 0.28 |
| Total | 100.0 | 289.69 | 100.0 |

[1]Commercially available from Corn Products in Westchester, IL as Erysta 3656 DC (80% erythritol)
[2]Commercially available from National Starch in Bridgewater, NJ
[3]Commercially available from International Flavors and Fragrances in New York, NY Example 3

Preparation of Bi-Sected Orally Disintegrating Tablet

A bi-sected orally disintegrating tablet having loratadine in one half-section and acetaminophen in the other half-section are manufactured as follows. 210.68 mg of the powder blend containing loratidine from Table 1 is dosed into a forming cavity. 289.69 mg of the powder blend containing acetaminophen from Table 2 is then dosed into the forming cavity using a physical separator to while dosing to prevent mixing into the loratidine blend. The tablet is then tamped to create a 625.65 mg tablet. The cavity is then activated with RF energy as described in Example 2 for approximately 2 to 5 seconds to form the orally disintegrating tablet and subsequently removed from the die block.

Example 4

Preparation of Bi-Sected Placebo Orally Disintegrating Tablet (ODT)

TABLE 3

Region 1 of Bi-Sected Placebo ODT

| Material | G/Batch | mg/tab region | Weight % |
|---|---|---|---|
| Dextrose Monohydrate, Fine powder | 64.54 | 129.08 | 64.54 |
| Sucralose | 0.15 | 0.30 | 0.15 |
| Vanilla Flavor[1] | 0.40 | 0.80 | 0.40 |
| Maltodextrin[2] | 34.89 | 69.78 | 34.89 |
| Blue #1 A1 Lake Colorant | 0.02 | 0.04 | 0.02 |
| TOTAL | 100.0 | 200.00 | 100.0 |

[1]Commercially available from the International Flavors and Fragrances Corporation in Hazlet, NJ
[2]Commercially available from National Starch in Bridgewater, NJ

TABLE 4

Region 1 of Bi-Sected Placebo ODT

| Material | G/Batch | mg/tab region | Weight % |
|---|---|---|---|
| Dextrose Monohydrate, Fine powder | 64.54 | 129.08 | 64.54 |
| Sucralose | 0.15 | 0.30 | 0.15 |
| Mint Flavor[1] | 0.40 | 0.80 | 0.40 |
| Maltodextrin[2] | 34.89 | 69.78 | 34.89 |
| Green Lake Colorant | 0.02 | 0.04 | 0.02 |
| TOTAL | 100.0 | 200.00 | 100.0 |

[1]Commercially available from the International Flavors and Fragrances Corporation in Hazlet, NJ
[2]Commercially available from National Starch in Bridgewater, NJ A bi-sected orally disintegrating placebo tablet having vanilla flavor and blue colorant in one region and green colorant and mint region in the other region is manufactured as follows. 200.0 mg of the powder blend from Table 3 is placed into the forming cavity. A physical separator is then placed within the die while dosing the second portion to prevent mixing into the first blend. 200.0 mg of the powder blend from Table 4 is then added into the forming cavity and tamped. The cavity is then activated with RF energy as described in Example 2 for approximately 2 to 5 seconds to form the orally disintegrating tablet at 400.0 mg and subsequently removed from the die block.

Example 5

Preparation of Bi-Sected Orally Disintegrating Tablet Via a Lyophillization Process Containing Loratidine and Phenylephrine A bi-sected orally disintegrating tablet having loratadine in one region and phenylephrine in the other region is manufactured as follows via a lyophillization process. Using the formula in Table 5, a solution is prepared while mixing in a suitable vessel. The gelatin, mannitol, flavorants, sucralose and colorant are added while mixing at approximately 50 RPM. After the gelatin is dissolved the loratidine is added and mixed. The resulting mixture is then deposited into a die in 161.07 portions. The contains a partition across the lateral section of the die to allow for deposition of the second portion. The first loratidine portion is dried and frozen and the partition is removed from the die. The second solution including phenylephrine is prepared utilizing the formula in Table 2 and the same mixing parameters as the loratidine solution. The phenyleprine solution is then added to the die containing the loratidine portion. The form is then dried and frozen, resulting in a bisected orally disintegrating tablet including loratidine in one portion and phenylephrine in a second portion.

TABLE 5

Region 1 of Bi-Sected Placebo ODT via Lyophillization

| Material | G/Batch | mg/tab region | Weight % |
|---|---|---|---|
| Mannitol | 54.0 | 6.00 | 27.00 |
| Gelatin | 54.0 | 6.00 | 27.00 |
| Peppermint Flavor[1] | 1.78 | 0.20 | 0.89 |
| Vanilla Flavor[1] | 0.44 | 0.05 | 0.22 |
| Loratidine | 88.00 | 10.00 | 44.00 |
| Sucralose | 1.78 | 0.20 | 0.89 |

TABLE 5-continued

Region 1 of Bi-Sected Placebo ODT via Lyophillization

| Material | G/Batch | mg/tab region | Weight % |
|---|---|---|---|
| Blue #1 A1 Lake Colorant | 0.09 | 0.01 | 0.04 |
| Purified Water | 1228.57 | a | N/A |
| TOTAL | 1429 | 22.55 | 100.0 | a - purified water removed upon drying
[1]Commercially available from the International Flavors and Fragrances Corporation in Hazlet, NJ

TABLE 6

Region 2 of Bi-region ODT via Lyophillization

| Material | G/Batch | mg/tab region | Weight % |
|---|---|---|---|
| Mannitol | 60.0 | 6.00 | 30.00 |
| Gelatin | 60.0 | 6.00 | 30.00 |
| Peppermint Flavor[1] | 2.00 | 0.20 | 1.00 |
| Vanilla Flavor[1] | 0.50 | 0.05 | 0.25 |
| Phenylephrine HCl | 75.16 | 7.50 | 37.58 |
| Sucralose | 2.00 | 0.20 | 1.00 |
| Blue #1 A1 Lake Colorant | 0.060 | 0.01 | 0.0005 |
| Purified Water | 1228.57 | a | N/A |
| TOTAL | 1428 | 19.96 | 100.0 | a - purified water removed upon drying
[1]Commercially available from the International Flavors and Fragrances Corporation in Hazlet, NJ

Example 6

Preparation of Bi-Sected Placebo Orally Disintegrating Tablet Via a Lyophillization Process A bi-sected placebo orally disintegrating tablet having is manufactured as follows via a lyophillization process. Using the formula in Table 7, a solution is prepared while mixing in a suitable vessel. The gelatin, mannitol, flavorants, sucralose and colorant are added while mixing at approximately 50 RPM. The resulting mixture is then deposited into a die in 161.07 portions. The contains a partition across the lateral section of the die to allow for deposition of the second portion. The first portion is dried and frozen and the partition is removed from the die. The second solution e is prepared utilizing the formula in Table 8 and the same mixing parameters as the first solution. 142.57 mg portions of the phenyleprine solution is then added to the die already containing the loratidine portion. The form is then dried and frozen, resulting in a bisected orally disintegrating tablet including blue colorant in one portion and no colorant in a second portion.

TABLE 7

Region 1 of Bi-Sected Placebo ODT via Lyophillization with Blue Colorant

| Material | G/Batch | mg/tab region | Weight % |
|---|---|---|---|
| Mannitol | 96.0 | 7.00 | 48.01 |
| Gelatin | 96.0 | 7.00 | 48.01 |
| Peppermint Flavor[1] | 3.42 | 0.25 | 1.71 |
| Vanilla Flavor[1] | 0.82 | 0.06 | 0.41 |
| Sucralose | 3.42 | 0.25 | 1.71 |

TABLE 7-continued

Region 1 of Bi-Sected Placebo ODT via Lyophillization with Blue Colorant

| Material | G/Batch | mg/tab region | Weight % |
|---|---|---|---|
| Blue #1 A1 Lake Colorant | 0.28 | 0.02 | 0.14 |
| Purified Water | 1228.14 | a | N/A |
| TOTAL | 1428 | 14.58 | 100.0 | a - purified water removed upon drying
[1]Commercially available from the International Flavors and Fragrances Corporation in Hazlet, NJ

TABLE 8

Region 2 of Bi-Sected Placebo ODT via Lyophillization without Colorant

| Material | G/Batch | mg/tab region | Weight % |
|---|---|---|---|
| Mannitol | 96.0 | 7.00 | 48.00 |
| Gelatin | 96.0 | 7.00 | 48.00 |
| Peppermint Flavor[1] | 3.44 | 0.25 | 1.72 |
| Vanilla Flavor[1] | 0.82 | 0.06 | 0.41 |
| Sucralose | 3.44 | 0.25 | 1.72 |
| Purified Water | 1228.57 | a | N/A |
| TOTAL | 1428 | 14.56 | 100.0 | a - purified water removed upon drying
[1]Commercially available from the International Flavors and Fragrances Corporation in Hazlet, NJ It is understood that while the invention has been described in conjunction with the detailed description thereof, that the foregoing description is intended to illustrate and not limit the scope of the invention, which is defined by the scope of the appended claims. Other aspects, advantages, and modifications are within the claims.

What is claimed is:

1. A method of manufacturing a solid dosage form, said method comprising the steps of:
    (a) measuring an amount of a first powder blend within a dosing nozzle, wherein said first powder blend comprises a pharmaceutically active agent;
    (b) discharging said measured amount of a first powder blend from said dosing nozzle into a forming cavity within a die block to obtain a volume of powder blend comprising at least said first powder blend within said forming cavity, said forming cavity having an inner wall, a first opening at the surface of one side of said die block, and a second opening at the surface on the opposite side of said die block;
    (c) moving a first forming tool into said forming cavity through the first opening of said forming cavity such that said volume of powder blend comprising at least said first powder blend is formed into the shape of said dosage form within said forming cavity between said inner wall, said first forming tool and a second forming tool within or adjacent to said cavity;
    (d) applying RF energy between a first electrode and a second electrode such that said energy heats said first powder blend within said forming cavity to form said dosage form; and
    (e) removing said dosage form from said forming cavity.

2. A method of claim 1, wherein said measured amount of said first powder blend is delivered to said dosing nozzle using negative pressure.

3. A method of claim 1, wherein said measured amount of said first powder blend is discharged from said dosing nozzle using positive pressure.

4. A method of claim 2, wherein said measured amount of said first powder blend is discharged from said dosing nozzle using positive pressure.

5. A method of claim 1, wherein said first powder blend has a density of less than 0.5 g/cc.

6. The method of claim 1, wherein said RF energy is applied at a frequency from about 1 MHz to about 50 MHz.

7. The method of claim 1, wherein said first RF electrode is operably associated with said first forming tool, said second RF electrode is operably associated with said second forming tool, and the portion of the inner wall of said forming cavity which is adapted to form said dosage form is insulative to said RF energy.

8. The method of claim 1, wherein one of said forming tools removes said dosage form from said forming cavity.

9. The method of claim 1, wherein said dosage form is placed into a blister card upon said removal from said forming cavity.

10. A method of manufacturing a solid dosage form, said method comprising the steps of:
   (a) measuring an amount of a first powder blend within a first dosing nozzle wherein said first powder blend comprises a pharmaceutically active agent;
   (b) discharging said measured amount of said first powder blend from said first dosing nozzle into a forming cavity within a die block to obtain a volume of powder blend comprising at least said first powder blend within said forming cavity, said forming cavity having an inner wall, a first opening at the surface of one side of said die block, and a second opening at the surface on the opposite side of said die block;
   (c) measuring an amount of a second powder blend within a second dosing nozzle;
   (d) discharging said measured amount of a second powder blend from said dosing nozzle into said forming cavity block to obtain a volume of powder blend comprising at least said first powder blend and said second powder blend within said forming cavity;
   (e) moving a first forming tool into said forming cavity through the first opening of said forming cavity such that said volume of powder blend comprising at least said first powder blend and said second powder blend are formed into the shape of said dosage form within said forming cavity between said inner wall, said first forming tool and a second forming tool within or adjacent to said cavity;
   (f) applying RF energy between a first electrode and a second electrode such that said energy heats at least said first powder blend within said forming cavity to form said dosage form; and
   (g) removing said dosage form from said forming cavity.

11. A method of claim 10, wherein said measured amount of said first powder blend is delivered to said first dosing nozzle using negative pressure and said measured amount of said second powder blend is delivered to said second dosing nozzle using negative pressure.

12. A method of claim 10, wherein said measured amount of said first powder blend is discharged from said dosing nozzle using positive pressure and said measured amount of said second powder blend is discharged from said second dosing nozzle using positive pressure.

13. A method of claim 11, wherein said measured amount of said first powder blend is discharged from said dosing nozzle using positive pressure and said measured amount of said second powder blend is discharged from said second dosing nozzle using positive pressure.

14. A method of claim 10, wherein said first powder blend has a density of less than 0.5 g/cc.

15. The method of claim 10, wherein said RF energy is applied at a frequency from about 1 MHz to about 50 MHz.

16. The method of claim 10, wherein said first RF electrode is operably associated with said first forming tool, said second RF electrode is operably associated with said second forming tool, and the portion of the inner wall of said forming cavity which is adapted to form said dosage form is insulative to said RF energy.

17. The method of claim 10, wherein one of said forming tools removes said dosage form from said forming cavity.

18. The method of claim 10, wherein said dosage form is placed into a blister card upon said removal from said forming cavity.

19. The method of claim 10, wherein said first powder blend and said second powder blend are added simultaneously to said forming cavity.

20. A method of manufacturing a solid dosage form, said method comprising the steps of:
   (a) measuring an amount of a first powder blend within a first dosing nozzle wherein said first powder blend comprises a pharmaceutically active agent;
   (b) discharging said measured amount of said first powder blend from said first dosing nozzle into a forming cavity within a die block, said forming cavity having an inner wall, a first opening at the surface of one side of said die block, and a second opening at the surface on the opposite side of said die block, wherein said forming chamber further comprises a movable divider adapted to form said first chamber and a second chamber within said forming cavity and said first powder blend is discharged into said first chamber;
   (c) measuring an amount of a second powder blend within a second dosing nozzle;
   (d) discharging said measured amount of said second powder blend from said dosing nozzle into said second chamber;
   (e) removing said movable divider from within said forming cavity such that said first powder blend contacts said second powder blend within said forming cavity;
   (f) moving a first forming tool into said forming cavity through the first opening of said forming cavity such that said first powder blend and said second powder blend are formed into the shape of said dosage form within said forming cavity between said inner wall, said first forming tool and a second forming tool within or adjacent to said cavity;
   (g) applying RF energy between said first electrode and said second electrode such that said energy heats said first powder blend within said forming cavity to form said dosage form; and
   (h) removing said dosage form from said forming cavity.

21. The method of claim 20, wherein said movable divider is non-linear.

* * * * *